(12) United States Patent
Larzon et al.

(10) Patent No.: US 12,690,850 B2
(45) Date of Patent: Jul. 28, 2026

(54) SELF-EXPANDING HEMOSTATIC DEVICES AND METHODS FOR FASCIA AND VESSEL PASSAGES

(71) Applicant: Arterica Inc., Santa Rosa, CA (US)

(72) Inventors: Thomas Larzon, Lidingö (SE); Cecilia Larzon, Stockholm (SE)

(73) Assignee: ARTERICA, INC, Santa Rosa, CA (US)

( * ) Notice: Subject to any disclaimer, the term of this patent is extended or adjusted under 35 U.S.C. 154(b) by 142 days.

(21) Appl. No.: 18/824,672

(22) Filed: Sep. 4, 2024

(65) Prior Publication Data

US 2024/0423597 A1     Dec. 26, 2024

Related U.S. Application Data

(62) Division of application No. 16/661,261, filed on Oct. 23, 2019, now Pat. No. 12,108,945.

(60) Provisional application No. 62/750,159, filed on Oct. 24, 2018.

(51) Int. Cl.
*A61B 17/00* (2006.01)

(52) U.S. Cl.
CPC .... *A61B 17/0057* (2013.01); *A61B 17/00491* (2013.01); *A61B 17/00234* (2013.01); *A61B 2017/0061* (2013.01); *A61B 2017/00619* (2013.01); *A61B 2017/00663* (2013.01); *A61B 2017/00862* (2013.01); *A61B 2017/00867* (2013.01)

(58) Field of Classification Search
CPC ........... A61B 2017/00672; A61B 2017/00663; A61B 17/0469
See application file for complete search history.

(56) References Cited

U.S. PATENT DOCUMENTS

| | | | |
|---|---|---|---|
| 5,108,421 | A | 4/1992 | Fowler |
| 5,364,408 | A | 11/1994 | Gordon |
| 5,391,183 | A | 2/1995 | Janzen et al. |
| 5,413,571 | A | 5/1995 | Katsaros et al. |
| 5,417,699 | A | 5/1995 | Klein et al. |
| 5,507,744 | A | 4/1996 | Tay et al. |
| 5,507,755 | A | 4/1996 | Gresl et al. |
| 5,540,704 | A | 7/1996 | Gordon et al. |
| 5,626,601 | A | 5/1997 | Gershony et al. |
| 5,700,273 | A | 12/1997 | Buelna et al. |

(Continued)

FOREIGN PATENT DOCUMENTS

| | | |
|---|---|---|
| EP | 2095774 | 9/2009 |
| EP | 2308521 | 4/2011 |

(Continued)

OTHER PUBLICATIONS

Non-Final Office Action Dated: May 20, 2025 in U.S. Appl. No. 18/213,636, filed Jun. 23, 2023 and published as: 2023-0329688 on Oct. 19, 2023.

(Continued)

*Primary Examiner* — Alexander J Orkin
(74) *Attorney, Agent, or Firm* — Schmeiser Olsen PLLC

(57) ABSTRACT

Self-expanding plug embodiments may be used in conjunction with vascular closure device embodiments to promote hemostasis at surgical sites or any other suitable location. In some cases, vascular closure device embodiments may include self-expanding plug embodiments in order to promote hemostasis at a surgical site during a vascular closure procedure.

13 Claims, 26 Drawing Sheets

(56) References Cited

U.S. PATENT DOCUMENTS

| | | | |
|---|---|---|---|
| 5,716,375 | A | 2/1998 | Fowler |
| 5,725,551 | A | 3/1998 | Meyers et al. |
| 5,728,134 | A | 3/1998 | Barak |
| 5,730,725 | A | 3/1998 | Yoon |
| 5,807,326 | A | 9/1998 | O'Neill et al. |
| 5,836,913 | A | 11/1998 | Orth et al. |
| 5,860,990 | A | 1/1999 | Nobles et al. |
| 5,868,762 | A | 2/1999 | Cragg et al. |
| 6,048,357 | A | 4/2000 | Kontos |
| 6,048,358 | A | 4/2000 | Barak |
| 6,059,800 | A | 5/2000 | Hart et al. |
| 6,077,279 | A | 6/2000 | Kontos |
| 6,110,184 | A | 8/2000 | Weadock |
| 6,231,561 | B1 | 5/2001 | Frazier et al. |
| 6,238,412 | B1 | 5/2001 | Dubrul et al. |
| 6,328,758 | B1 | 12/2001 | Tornier et al. |
| 6,436,088 | B2 | 8/2002 | Frazier |
| 6,461,366 | B1 | 10/2002 | Seguin |
| 6,562,052 | B2 | 5/2003 | Nobles |
| 6,626,918 | B1 | 9/2003 | Ginn et al. |
| 6,626,930 | B1 | 9/2003 | Allen et al. |
| 6,669,719 | B2 | 12/2003 | Wallace et al. |
| 7,458,978 | B1 | 12/2008 | Bender et al. |
| 7,789,893 | B2 | 9/2010 | Drasler et al. |
| 8,252,005 | B2 | 8/2012 | Findlay, III et al. |
| 8,414,528 | B2 | 4/2013 | Liu et al. |
| 8,617,204 | B2 | 12/2013 | Khosravi et al. |
| 8,821,532 | B2 | 9/2014 | Schaeffer |
| 8,920,442 | B2 | 12/2014 | Sibbitt, Jr. et al. |
| 9,017,374 | B2 | 4/2015 | Yassinzadeh |
| 9,687,216 | B2 | 6/2017 | Sawhney et al. |
| 9,782,156 | B2 | 10/2017 | Larzon et al. |
| 11,375,994 | B2 | 7/2022 | Fortson |
| 12,508,011 | B2 | 12/2025 | Larzon |
| 2002/0026208 | A1 | 2/2002 | Roe et al. |
| 2002/0045908 | A1 | 4/2002 | Nobles et al. |
| 2002/0077581 | A1 | 6/2002 | Davidner et al. |
| 2003/0233120 | A1 | 12/2003 | Akerfeldt |
| 2004/0087967 | A1 | 5/2004 | Schur et al. |
| 2004/0097978 | A1 | 5/2004 | Modesitt et al. |
| 2005/0121042 | A1 | 6/2005 | Belhe et al. |
| 2005/0149066 | A1 | 7/2005 | Stafford |
| 2005/0155608 | A1 | 7/2005 | Pavcnik et al. |
| 2005/0251155 | A1 | 11/2005 | Orban |
| 2005/0267528 | A1 | 12/2005 | Ginn et al. |
| 2006/0069397 | A1 | 3/2006 | Nobles et al. |
| 2006/0089627 | A1 | 4/2006 | Burnett et al. |
| 2006/0135991 | A1 | 6/2006 | Kawaura et al. |
| 2006/0142784 | A1 | 6/2006 | Kontos |
| 2007/0049967 | A1 | 3/2007 | Sibbitt, Jr. et al. |
| 2007/0083231 | A1 | 4/2007 | Lee |
| 2007/0112425 | A1 | 5/2007 | Schaller et al. |
| 2007/0203506 | A1 | 8/2007 | Sibbitt, Jr. et al. |
| 2007/0203507 | A1 | 8/2007 | McLaughlin et al. |
| 2007/0213616 | A1 | 9/2007 | Anderson et al. |
| 2007/0276413 | A1 | 11/2007 | Nobels |
| 2008/0082122 | A1 | 4/2008 | Khosravi et al. |
| 2008/0097509 | A1 | 4/2008 | Beyar et al. |
| 2008/0147112 | A1 | 6/2008 | Sheets et al. |
| 2008/0154303 | A1 | 6/2008 | Yassinzadeh |
| 2008/0177288 | A1 | 7/2008 | Carlson |
| 2008/0287988 | A1 | 11/2008 | Smith et al. |
| 2008/0294001 | A1 | 11/2008 | Surti |
| 2008/0300629 | A1 | 12/2008 | Surti |
| 2009/0143808 | A1 | 6/2009 | Houset |
| 2009/0248056 | A1 | 10/2009 | Gabel et al. |
| 2009/0254110 | A1 | 10/2009 | Bagaoisan et al. |
| 2009/0254119 | A1 | 10/2009 | Sibbitt, Jr. et al. |
| 2009/0264922 | A1 | 10/2009 | Mas |
| 2009/0306685 | A1 | 12/2009 | Fill |
| 2009/0318936 | A1 | 12/2009 | Harris et al. |
| 2010/0042118 | A1 | 2/2010 | Garrison et al. |
| 2010/0179572 | A1 | 7/2010 | Voss et al. |
| 2010/0179590 | A1 | 7/2010 | Fortson et al. |
| 2010/0217308 | A1 | 8/2010 | Hanson |
| 2010/0217311 | A1 | 8/2010 | Jenson et al. |
| 2010/0217312 | A1 | 8/2010 | Hill et al. |
| 2010/0262166 | A1 | 10/2010 | Boraiah et al. |
| 2011/0077668 | A1 | 3/2011 | Gordon et al. |
| 2011/0218568 | A1 | 9/2011 | Voss |
| 2011/0238090 | A1 | 9/2011 | Heneveld |
| 2011/0301619 | A1 | 12/2011 | Walters |
| 2012/0010633 | A1 | 1/2012 | Noda et al. |
| 2012/0158045 | A1 | 6/2012 | Pipenhagen |
| 2012/0290001 | A1 | 11/2012 | Uchida et al. |
| 2012/0296373 | A1 | 11/2012 | Roorda et al. |
| 2013/0006297 | A1 | 1/2013 | Drasler |
| 2013/0123812 | A1 | 5/2013 | Tegels |
| 2013/0123844 | A1 | 5/2013 | White |
| 2013/0190812 | A1 | 7/2013 | Vidlund |
| 2013/0231701 | A1 | 9/2013 | Voss et al. |
| 2014/0039547 | A1 | 2/2014 | White |
| 2014/0076955 | A1 | 3/2014 | Lorenz |
| 2014/0214079 | A1 | 7/2014 | Ewers et al. |
| 2014/0257359 | A1 | 9/2014 | Tegels et al. |
| 2015/0005810 | A1 | 1/2015 | Center et al. |
| 2015/0066055 | A1 | 3/2015 | Sibbitt, Jr. et al. |
| 2015/0105805 | A1 | 4/2015 | Fortson |
| 2015/0142049 | A1 | 5/2015 | Delgado et al. |
| 2015/0265350 | A1 | 9/2015 | Shimizu et al. |
| 2015/0289861 | A1 | 10/2015 | MacPhee et al. |
| 2016/0228107 | A1 | 8/2016 | Madsen et al. |
| 2016/0228109 | A1 | 8/2016 | Jacobs et al. |
| 2016/0242793 | A1 | 8/2016 | Norton et al. |
| 2017/0049426 | A1 | 2/2017 | Gianotti et al. |
| 2017/0049570 | A1 | 2/2017 | O'Beirne et al. |
| 2017/0086804 | A1 | 3/2017 | Larzon et al. |
| 2017/0086807 | A1 | 3/2017 | Larzon et al. |
| 2017/0203082 | A1 | 7/2017 | Foy et al. |
| 2017/0325794 | A1 | 11/2017 | Willard et al. |
| 2018/0049731 | A1 | 2/2018 | Hardy et al. |
| 2019/0142402 | A1 | 5/2019 | Larzon et al. |
| 2019/0142403 | A1 | 5/2019 | Nyman et al. |
| 2019/0240023 | A1 | 8/2019 | Spence et al. |
| 2020/0046343 | A1 | 2/2020 | Kramer |
| 2020/0129164 | A1 | 4/2020 | Larzon et al. |
| 2020/0155817 | A1 | 5/2020 | Kassab et al. |
| 2023/0309979 | A1 | 10/2023 | Agnihotri et al. |
| 2023/0310155 | A1 | 10/2023 | Coumane |
| 2024/0138824 | A1 | 5/2024 | Hauck et al. |

FOREIGN PATENT DOCUMENTS

| | | |
|---|---|---|
| EP | 2656816 | 10/2013 |
| EP | 4169453 A1 | 4/2023 |
| GB | 2365342 | 2/2002 |
| JP | 2005-511130 | 4/2005 |
| JP | 2013-226414 | 11/2013 |
| WO | WO 96/024291 | 8/1996 |
| WO | WO 97/03613 | 2/1997 |
| WO | WO 24/092233 | 5/2004 |
| WO | WO 19/157022 | 8/2009 |
| WO | WO 10/081103 | 7/2010 |
| WO | WO 14/169215 | 10/2014 |
| WO | WO 17/019525 | 2/2017 |
| WO | WO 18/195274 | 10/2018 |
| WO | WO 19/098921 | 5/2019 |
| WO | WO 19/098922 | 5/2019 |
| WO | WO 20/081864 | 4/2020 |
| WO | WO 20/085983 | 4/2020 |
| WO | WO 23/072972 | 5/2023 |

OTHER PUBLICATIONS

Bountouris et al., "Endovascular aneurysm repair with Fascia suture technique: short and mid-term results," Int Angiol, Epub Nov. 10, 2015.

Fisher, "The Fascia Suture Technique: This Late Bloomer Could Become a Winner," J. Endovasc Ther, 2012, 19:397-399.

Freitas et al., "The use of closure devices in peripheral endovascular interventions: The Leipzig real-world report," Journal of The American College of Cardiology, TCT Abstracts/Vascular Access and

(56) References Cited

OTHER PUBLICATIONS

Intervention—Femoral (includes closure devices) Abstract TCT-842, p. B245, Saturday, Sep. 13, 2014, 5:00 PM-7:00 Pm.

Harrison et al., "Fascial Closure Following Percutaneous Endovascular Aneurysm Repair," Eur J Vasc Endovasc Surg (2011) 41, 346-349.

Larzon et al., "Editor's Choice—A Randomized Controlled Trial of the Fascia Suture Technique Compared with a Suture-mediated Closure Device for Femoral Arterial Closure after Endovascular Aortic Repair," Eur J Vasc Endovasc Surg (Feb. 2015) 49, 166-173.

Larzon et al., "Fascia Suturing of Large Access Sites After Endovascular Treatment of Aortic Aneurysms and Dissections," J Endovasc Ther, 2006, 13:152-157.

Lee et al., "Midterm outcomes of femoral arteries after percutaneous endovascular aortic repair using the Preclose technique," J Vasc Surg, 2008: 47:919-923.

Mathisen et al., "Complication Rate of the Fascia Closure Technique in Endovascular Aneurysm Repair," J Endovasc Ther 2012; 19:392-396.

Montan et al., "Short- and Midterm Results of the Fascia Suture Technique for Closure of Femoral Artery Access Sites After Endovascular Aneurysm Repair," J Endovasc Ther, 2011; 18:789-796.

Nelson, "Closure and Arterial Access Conundrums" Presentat+A25ion, Saturday Jun. 7, 2014, Society for Vascular Surgery, 2014 Vascular Annual Meeting, Boston, Jun. 5-7.

Wanhainen, A., "Invited Commentary, Commentary on 'A Randomized Controlled Trial of the Fascia Suture Technique Compared with a Suture-mediated Closure Device for Femoral Arterial Closure After Endovascular Aortic Repair'" Eur J Vasc Endovasc Surg (Feb. 2015) 49, 174-174.

International Search Report and Written Opinion dated: Jan. 31, 2017 in International Application No. PCT/IB2016/001498 filed: Sep. 27, 2016.

Non Final Office Action dated: Dec. 15, 2016 in U.S. Appl. No. 15/291,991 , filed Oct. 12, 2016, published as US-2017/0086807 on Mar. 30, 2017.

Notice of Allowance dated: May 12, 2017 in U.S. Appl. No. 15/291,991, filed Oct. 12, 2016, published as US-2017/0086807 on Mar. 30, 2017.

Notice of Allowance dated: Nov. 20, 2018 in U.S. Appl. No. 15/611,665, filed Jun. 1, 2017, published as: 2017-0265848 on Sep. 21, 2017.

Notice of Allowance dated: Sep. 19, 2018 in U.S. Appl. No. 15/611,665, filed Jun. 1, 2017, published as: 2017-0265848 on Sep. 21, 2017.

Final Office Action dated: Jan. 10, 2018 in U.S. Appl. No. 15/611,665, filed Jun. 1, 2017, published as: 2017-0265848 on Sep. 21, 2017.

Non-Final Office Action dated: Aug. 9, 2017 in U.S. Appl. No. 15/611,665, filed Jun. 1, 2017, published as: 2017-0265848 on Sep. 21, 2017.

Non-Final Office Action dated: Aug. 16, 2022 in U.S. Appl. No. 16/836,609, filed Mar. 31, 2020, published as: 2020-0245987 on Aug. 6, 2020.

Non-Final Office Action dated: Aug. 30, 2018 in U.S. Appl. No. 15/277,542, filed Sep. 27, 2016 published as 2017-0086804 on Mar. 30, 2017.

Final Office Action dated: Apr. 24, 2019 in U.S. Appl. No. 15/277,542, filed Sep. 27, 2016 published as 2017-0086804 on Mar. 30, 2017.

Final Office Action dated: Oct. 3, 2019 in U.S. Appl. No. 15/277,542, filed Sep. 27, 2016 published as 2017-0086804 on Mar. 30, 2017.

Notice of Allowance dated: Jan. 2, 2020 in U.S. Appl. No. 15/277,542, filed Sep. 27, 2016 published as 2017-0086804 on Mar. 30, 2017.

International Search Report and Written Opinion dated: Feb. 13, 2019 in International Application No. PCT/SE2018/051173 filed: Nov. 14, 2018.

International Search Report and Written Opinion dated: Feb. 12, 2019 in International Application No. PCT/SE2018/051172 filed: Nov. 14, 2018.

Extended European Search Report dated: May 13, 2019 in European Patent Application No. EP16850451.2 based on International Patent Application PCT/IB2016/001498 filed: Sep. 27, 2016 and published as: EP3355803 on Aug. 8, 2018.

International Search Report and Written Opinion dated: Jan. 28, 2020 in International Application No. PCT/SE2018/051041 filed: Oct. 23, 2019.

Invitation to Pay Additional Fees dated: Jan. 25, 2021 in International Application No. PCT/US2020/061117 filed: Nov. 18, 2020.

Non-Final Office Action Dated: Mar. 17, 2021 in U.S. Appl. No. 16/190,654, filed Nov. 14, 2018 and published as: 2019-0142402 on May 16, 2019.

International Preliminary Report on Patentability dated: Jun. 2, 2022 in International Application No. PCT/US2020/061117 filed: Nov. 18, 2020 and published as: WO/2021/102044 on May 27, 2021.

International Search Report and Written Opinion dated: Mar. 26, 2021 in International Application No. PCT/US2020/061117 filed: Nov. 18, 2020.

Non-Final Office Action dated: Feb. 8, 2021 in U.S. Appl. No. 16/190,694, filed Nov. 14, 2018 published as: 2019-0142403 on: May 16, 2019.

Final Office Action dated: Aug. 4, 2021 in U.S. Appl. No. 16/190,694, filed Nov. 14, 2018 and published as: 2019/0142403 on: May 16, 2019.

Non-Final Office Action dated: Nov. 18, 2021 in U.S. Appl. No. 16/190,694, filed Nov. 14, 2018 and published as: 2019/0142403 on: May 16, 2019.

Non-Office Action dated: Jul. 13, 2022 in U.S. Appl. No. 16/190,694, filed Nov. 14, 2018 and published as: 2019/0142403 on: May 16, 2019.

Notice of Allowance and Corrected Notice of Allowability Dated: Aug. 30, 2021 in U.S. Appl. No. 16/190,654, filed Nov. 14, 2018 and published as: 2019-0142402 on May 16, 2019.

Final Office Action dated: Sep. 13, 2023 in U.S. Appl. No. 16/661,261, filed Oct. 23, 2019 and published as: 2020/0129164 on: Apr. 30, 2020.

Non-Final Office Action dated: Jan. 4, 2023 in U.S. Appl. No. 16/661,261, filed Oct. 23, 2019 and published as: 2020/0129164 on: Apr. 30, 2020.

Final Office Action dated: Sep. 7, 2022 in U.S. Appl. No. 16/661,261, filed Oct. 23, 2019 and published as: 2020/0129164 on: Apr. 30, 2020.

Non-Final Office Action dated: Mar. 15, 2022 in U.S. Appl. No. 16/661,261, filed Oct. 23, 2019 and published as: 2020/0129164 on: Apr. 30, 2020.

Non-Final Office Action dated: Jan. 31, 2024 in U.S. Appl. No. 16/661,261, filed Oct. 23, 2019 and published as: 2020/0129164 on: Apr. 30, 2020.

Notice of Allowance dated: Jun. 12, 2024 in U.S. Appl. No. 16/661,261, filed Oct. 23, 2019 and published as: 2020/0129164 on: Apr. 30, 2020.

Extended European Search Report dated: Jul. 11, 2022 in European Patent Application No. EP19875930.0 filed as: PCT/SE2019/051041 on: Oct. 23, 2019.

Notice of Allowance dated: Nov. 14, 2023 in U.S. Appl. No. 16/951,886, filed Nov. 18, 2020 and published as: 2021/0145421 on May 20, 2021.

Invitation to Pay Additional Fees dated: Feb. 20, 2024 in International Application No. PCT/US2023/078087 filed: Oct. 27, 2023.

International Search Report and Written Opinion dated: Apr. 10, 2024 in International Application No. PCT/US2023/078087 filed: Oct. 27, 2023 and published as: WO/2024/092233 on May 2, 2024.

Non-Final Office Action Dated: May 22, 2024 in U.S. Appl. No. 17/507,640, filed Oct. 21, 2021 and published as: 2022-0039781 on Feb. 10, 2022.

Extended European Search Report dated May 22, 2024 in European Patent Application No. 20891101.6 filed: Nov. 18, 2020.

Non-Final Office Action Dated: Aug. 8, 2024 in U.S. Appl. No. 18/538,926, filed Dec. 13, 2023 and published as: 2024-0108321 on Apr. 4, 2024.

(56) References Cited

OTHER PUBLICATIONS

Non-Final Office Action dated: Jan. 20, 2026 in U.S. Appl. No. 18/496,641, field Oct. 27, 2023 and published as: 2024-0138824 on: May 2, 2024.
Notice of Allowance dated: Feb. 20, 2026 in U.S. Appl. No. 18/431,814, filed Feb. 2, 2024 and published as: 2024-0173527 on: May 30, 2024.

SELF-EXPANDING HEMOSTATIC DEVICES AND METHODS FOR FASCIA AND VESSEL PASSAGES

RELATED APPLICATIONS

The present application is a divisional of co-pending U.S. patent application Ser. No. 16/661,261, filed Oct. 23, 2019, by Thomas LARZON et al., titled "SELF-EXPANDING HEMOSTATIC DEVICES AND METHODS FOR FASCIA AND VESSEL PASSAGES", which claims priority from U.S. Provisional Patent Application No. 62/750,159, filed Oct. 24, 2018, by Thomas LARZON et al., titled "SELF-EXPANDABLE HEMOSTATIC DEVICE FOR FASCIA AND VESSEL WALL", each of which is incorporated by reference herein in its entirety.

BACKGROUND

During use of a vascular closure device, it is relatively common to have some minor bleeding from the access site while using the vascular closure device. This can normally be handled by simultaneous manual compression but a possible disadvantage of that technique may be that it occupies the use of one hand of the operator or requires the assistance of a second operator. Even though it is not proven that the minor bleeding is clinically significant or requires further resources from the health care system, this is an undesirable situation as it complicates the procedure and may cause concern on behalf of the patient. An established principle to control bleeding from the vessel is to inflate a balloon inside the vessel at the access hole in the vessel. This may, however, interfere with calcification on the inside of a calcified vessel, possibly causing ruptures of a plaque with subsequent risk for thromboses. It may also interfere with the mechanism of some vascular closure device embodiments. Embodiments discussed herein may be useful to reduce the chance of peri-procedural bleeding during use of a vascular closure device.

SUMMARY

Some embodiments of a vascular closure device may include an outer housing having an elongate configuration with an axial length greater than a transverse dimension thereof, a proximal end, a distal end, an inner lumen extending from the proximal end to the distal end, and a distal section. The vascular closure device may also include a plurality of anchor deployers which are slidably disposed within the outer housing adjacent each other at the distal section of the outer housing and which are configured to extend and spread from the distal section of the outer housing. Each of the anchor deployers may include a deployment rod which is slidably disposed relative to the outer housing and which includes an elongate resilient configuration and a distal end that extends from the distal section of the outer housing. Each of the anchor deployers may also include an anchor which is removably secured to the distal end of the deployment rod and which is configured to penetrate tissue in a distal direction. In addition, a filament may be slidably disposed within the housing and include a distal end which is secured to the anchor. The vascular closure device may also include a tissue grip which is deployable from the distal end of the outer housing and which may be configured to secure tissue portions in fixed relation to each other. The vascular closure device may also include an inner hemostatic assembly that includes an elon-gate shaft having an axial length greater than a transverse dimension thereof, a proximal end, a distal end and a distal section that is axially slidable within the inner lumen of the outer housing. The inner hemostatic assembly may also include a self-expanding plug which is disposed on the distal section of the elongate shaft proximal of the distal end of the elongate shaft, the self-expanding plug including an outer profile that is configured to self-expand from a compressed state sized to fit within the inner lumen of the outer housing to an expanded state with an outer transverse dimension which is larger than an outer transverse dimension of the elongate shaft and which is configured to plug an access hole in a wall of a blood vessel of a patient so as to reduce or eliminate leakage of blood therefrom.

Some embodiments of a method for vascular closure may include advancing an elongate shaft of an inner hemostatic assembly of a vascular closure device over a guidewire and through a passage in a tissue layer which is disposed adjacent an access hole in a wall of a patient's blood vessel. The elongate shaft may be so advanced until a distal end of the elongate shaft is disposed within the patient's vessel and a self-expanding plug disposed on a distal section of the elongate shaft is disposed within the access hole in an expanded state and is reducing leakage of blood from the access hole. The method may further include positioning a distal end of an outer housing of the vascular closure device adjacent the passage in the tissue layer and deploying a plurality of anchor deployers from a distal section of the outer housing of the vascular closure device and engaging the tissue layer in positions disposed about the passage in the tissue layer with respective anchors of the plurality of anchor deployers. The method may further include securing the anchors to the tissue layer in the positions disposed about the passage in the tissue layer and drawing the anchors closer together with filaments secured to each of the anchors so as to draw the anchors and respective portions of the tissue layer secured to each of the anchors together thereby reducing the passage in the tissue layer. Thereafter, the inner hemostatic assembly may be withdrawn from the patient's vessel and into the inner lumen of the outer housing until the elongate shaft is no longer disposed within the access hole of the vessel or passage of the tissue layer. A tissue grip may be deployed to secure the portions of the tissue layer which have been drawn together thereby closing the passage in the tissue layer and achieving vascular closure of the access hole in the blood vessel.

Some embodiments of a vascular closure device may include an outer housing having an elongate configuration with an axial length greater than a transverse dimension thereof, a proximal end, a distal end, an inner lumen extending from the proximal end to the distal end, and a distal section. The vascular closure device may also include a plurality of anchor deployers which are slidably disposed within the outer housing adjacent each other at the distal section of the outer housing and which are configured to extend and spread from the distal section of the outer housing. The vascular closure device may also include an inner hemostatic assembly that includes an elongate shaft having an axial length greater than a transverse dimension thereof, a proximal end, a distal end and a distal section that is axially slidable within the inner lumen of the outer housing. The inner hemostatic assembly may also include a self-expanding plug which is disposed on the distal section of the elongate shaft proximal of the distal end of the elongate shaft, the self-expanding plug including an outer profile that is configured to self-expand from a compressed state sized to fit within the inner lumen of the outer housing to an expanded state with an outer transverse dimension which is larger than an outer transverse dimension of the elongate shaft and which is configured to plug an access hole in a wall of a blood vessel of a patient so as to reduce or eliminate leakage of blood therefrom.

Certain embodiments are described further in the following description, examples, claims and drawings. These features of embodiments will become more apparent from the following detailed description when taken in conjunction with the accompanying exemplary drawings.

The drawings are intended to illustrate certain exemplary embodiments and are not limiting. For clarity and ease of illustration, the drawings may not be made to scale, and in some instances, various aspects may be shown exaggerated or enlarged to facilitate an understanding of particular embodiments.

DETAILED DESCRIPTION

As discussed above, after a minimally invasive vascular procedure, such as a catheterization procedure, a residual hole in the form of an access hole or the like may remain in a major vessel at an access site. Methods for percutaneous closure or sealing of such an access hole may include remote suturing of the vessel, plugging the hole, and remote suturing of the fascia adjacent to the vessel. Certain device and method embodiments discussed herein are directed to mechanical closure of an access passage in the fascia tissue layer adjacent to an access hole in a vessel such as an artery or vein of a patient. Some of these embodiments may also be applicable to direct closure of an arterial wall in some instances. Some vascular closure device and method embodiments discussed herein may provide a robust and convenient device for closing a vascular access hole after a minimally invasive procedure. In some cases, vascular closure device embodiments discussed herein may be useful for closing large vascular access holes. In addition, certain vascular closure device and method embodiments are discussed in U.S. patent application Ser. No. 15/277,542, filed Sep. 27, 2016, by Thomas Larzon, et al., entitled VASCU- LAR CLOSURE DEVICE, U.S. patent application Ser. No. 16/190,654, filed Nov. 14, 2018, by Thomas Larzon, et al., entitled COLLAPSIBLE TUBE FOR HEMOSTASIS, and U.S. patent application Ser. No. 16/190,694, filed Nov. 14, 2018, by Henrik Nyman, et al., entitled TISSUE CLOSURE DEVICE, each of which is incorporated by reference herein in its entirety.

Figure 1:
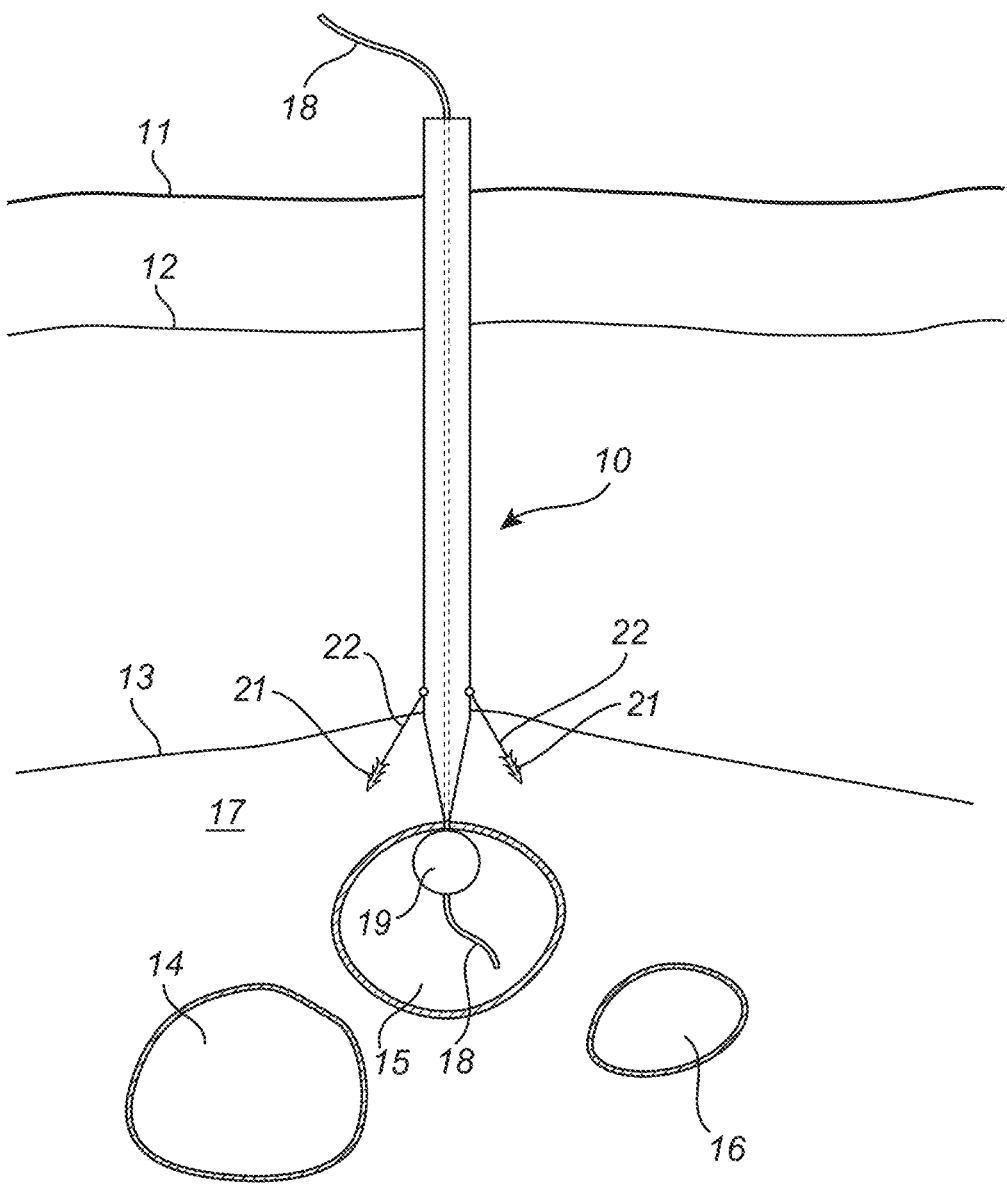
FIG. 1 shows a schematic view of vascular closure device embodiment.

The following discussion of the device and method embodiments of FIGS. 1-4B is directed generally to closure of a vascular access passage as well as axial positioning of certain portions of vascular closure device embodiments during such a closure procedure. Such axial positioning devices and methods may be applied to and used with any other appropriate vascular closure device or method embodiments discussed herein. Referring to FIG. 1, an embodiment of a vascular closure device 10 is introduced percutaneously over a guide wire 18 into a blood vessel/artery 15, through the skin 11 and the fascia lata 12 of a patient. An optional anvil member 19 may be arranged inside the blood vessel 15 to create a reference point along an axial orientation to the engagement members 21 and/or for controlling bleeding from an inner lumen of the artery 15.

The engagement members 21 may then be placed and released through the vascular closure device 10 and may attach to fascia tissue 13 proximate to the blood vessel 15 and may involve the fascia membrane 13 (fascia iliacus), but, in some instances, not a wall 32 of the blood vessel 15. The engagement members 21 may for example be pushed out of the vascular closure device 10 and into the fascia membrane 13 using deployment members provided as pusher rods 22 arranged in independent lumens provided with the vascular closure device 10, for example through a pusher assembly in a common lumen that simultaneously deploys all engagement members 21, through a spring-loaded mechanism or the like. For some embodiments, the engagement members 21 may be connected with a single filament such as a suture or a plurality of filaments or sutures 23 shown in FIGS. 2A and 2B. In FIG. 1 there is further shown a femoral vein 14, a femoral nerve 16 and adjacent/interstitial tissues 17.

Figures 2A, 2B, 2C, 2D:
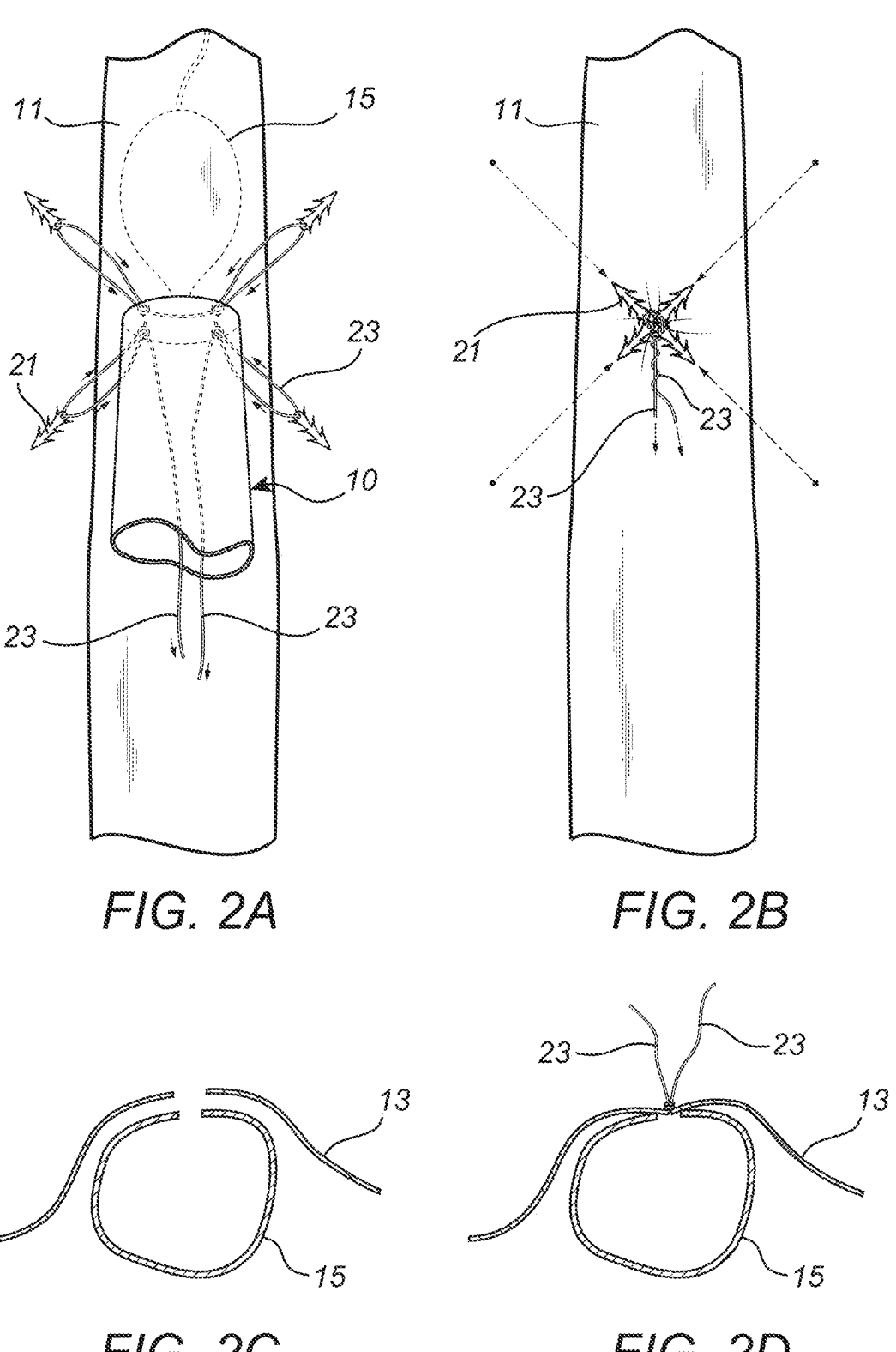
FIGS. 2A and 2B show a sequence depicting the creation of a tissue lock using the vascular closure device embodiment shown in FIG. 1.
FIGS. 2C and 2D illustrate a vascular closure method sequence for treatment of a passage through a wall of a blood vessel without directly engaging the blood vessel.

With further reference to FIGS. 2A and 2B, the suture 23 may for example be routed through each of the engagement members 21 in sequence. In particular, one suture 23 may be looped through each of the engagement members 21 in sequence, or a separate suture 23 may be attached to each engagement member 21. The tissue, e.g. fascia membrane 13, may then pulled together in a radially inward direction towards an access passage in the fascia layer 13 with the suture 23 connected to the engagement members 21. When pulled together, the tissue/fascia membrane 13 is tightened towards the center and the access passage therethrough and may then create a tissue lock, thereby indirectly sealing the access hole in the artery 15. That is, a distance between the initial position of the engagement members 21 and a distance between the engagement members once the engagement members 21 have been moved radially inward towards each other is thereby reduced. When tightening the fascia membrane 13 the anvil member 19 may be removed from the artery 15.

Referring to FIGS. 2C and 2D, an embodiment of a vascular closure sequence is shown whereby a passage through a wall 32 of the vessel 15 such as the blood vessel shown is treated such that leakage of blood from the interior volume of the blood vessel (not shown) is stopped or slowed to a clinically acceptable degree. As seen in FIG. 2C, a hole in the wall of the blood vessel, specifically, the femoral artery 15, is disposed in general alignment with a passage through the fascia tissue layer 13 disposed proximate to an outer surface of the femoral artery 15. For this particular exemplary embodiment, the tissue layer disposed outside of and proximate to the outer surface of the femoral artery 15 is the fascia iliacus 13. For purposes of this general discussion, the phrase "in general alignment" as applied to the respective passages may mean at least that an appropriately sized elongate device such as a catheter or sheath may pass through both passages without significant relative lateral displacement between the tissue 13 and artery 15.

In addition, in some cases, the tissue layer 13 may be disposed sufficiently proximate the outside surface of the blood vessel 15 such that gathering and approximation of the fascia tissue 13 which is disposed about the passage through the tissue 13 so as to close the passage through the tissue/fascia membrane 13 and form a tissue lock is sufficient to tighten and displace the closed gathered tissue/fascia membrane 13 against the outer surface of the artery 15 which is adjacent the passage through the artery 15 as shown in FIG. 2D.

When the gathered tissue 13 has been displaced and deflected so as to be disposed against the passage of the artery 15 and wall of the artery 15 disposed about the passage in the artery 15, this mechanical approximation will typically be sufficient in order to achieve a clinically sufficient slowing or stoppage of blood leakage from the passage in the artery 15 in order to permit closure of an access site through the patient's skin 1 adjacent the passages. In some instances, an inner surface of the tissue layer 13 disposed proximate to the outer surface of the blood vessel 15 may be separated from the outer surface of the blood vessel in the region of the respective passages therethrough by a distance of up to about 10 mm, more specifically, up to about 5 mm.

Figure 3A:
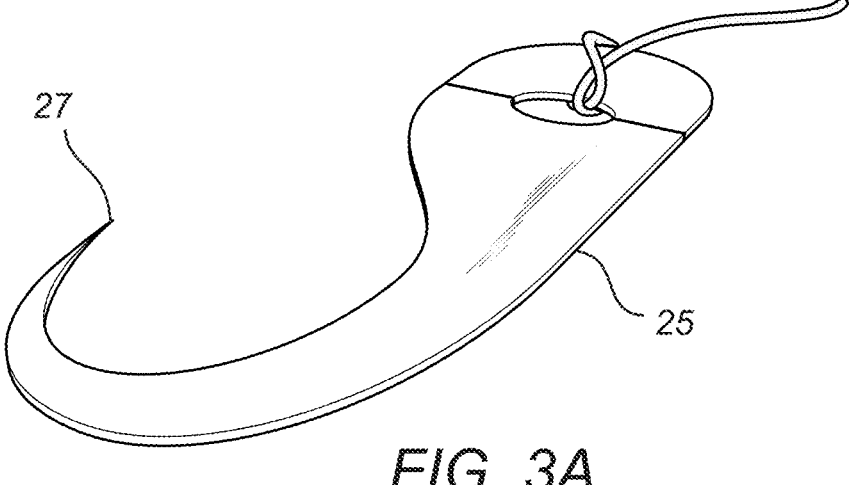
FIGS. 3A and 3B illustrate an engagement member embodiment, exemplified as an anchor element.
Figure 3B:
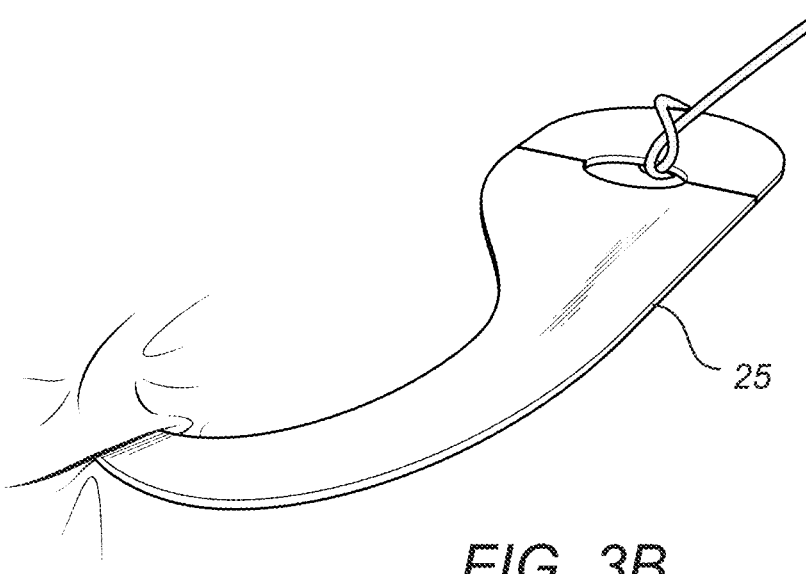

With further reference to FIGS. 3A and 3B, there is conceptually illustrated an engagement member, exemplified as an anchor element 25. In FIG. 3A, the anchor element 25 is shown as initially deployed, so that it slides easily in the direction away from a deployment point. Note that the deployment point may optionally be deflected toward the tissue/fascia membrane 13 to promote engagement. FIG. 3B shows the anchor element 25 after motion has been reversed toward the deployment point, and the anchor element 25 has embedded into the tissue/fascia membrane 13. That is, a tip 27 of the anchors element 25 is in one embodiment hook-shaped, so that it easily slides outward without engaging the tissue/fascia membrane 13. However, once the anchor element 25 is retracted, at least the tip 27 of the anchor element 25 is adapted to mechanically engage with the tissue/fascia membrane 13.

Figure 4A:
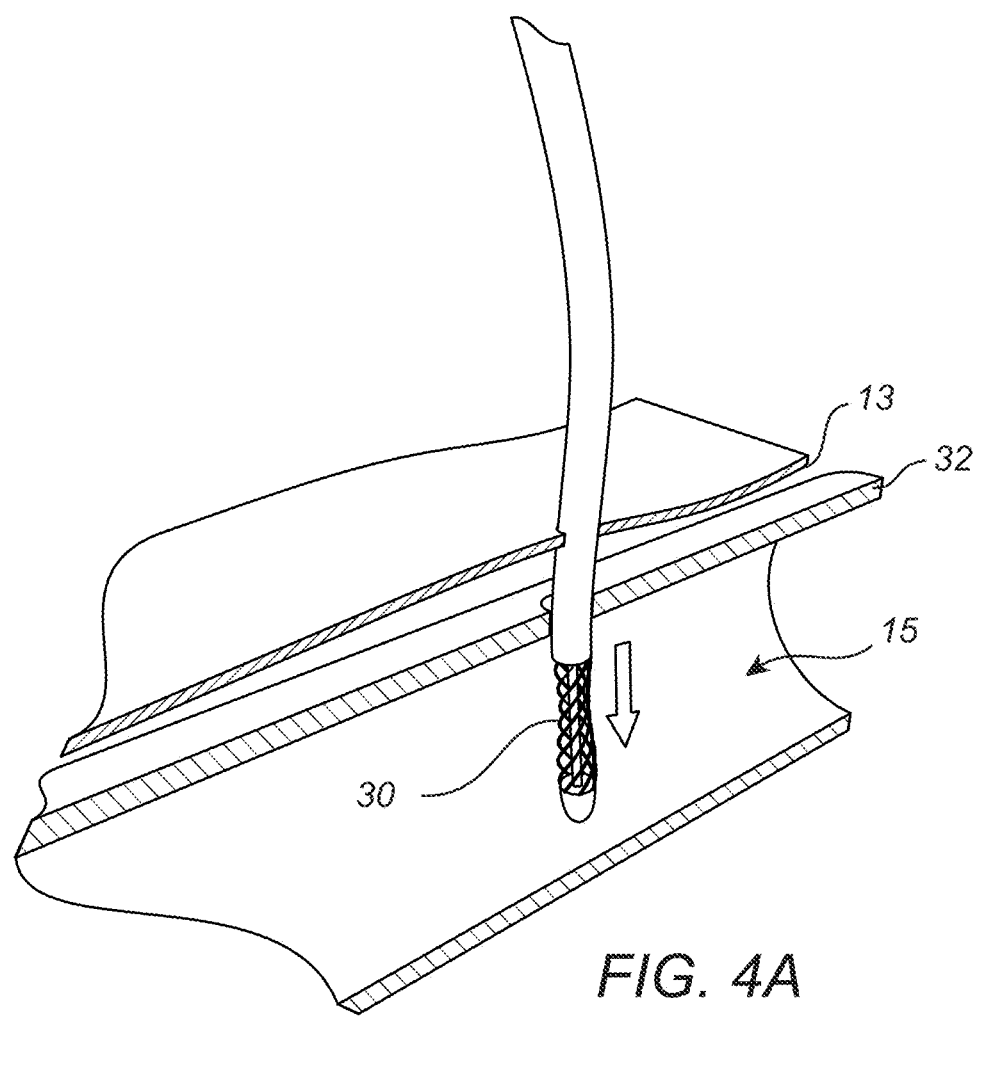
FIGS. 4A and 4B illustrate the operation of an anvil member embodiment of a vascular closure device embodiment that may function as a deployable positioning feature.
Figure 4B:
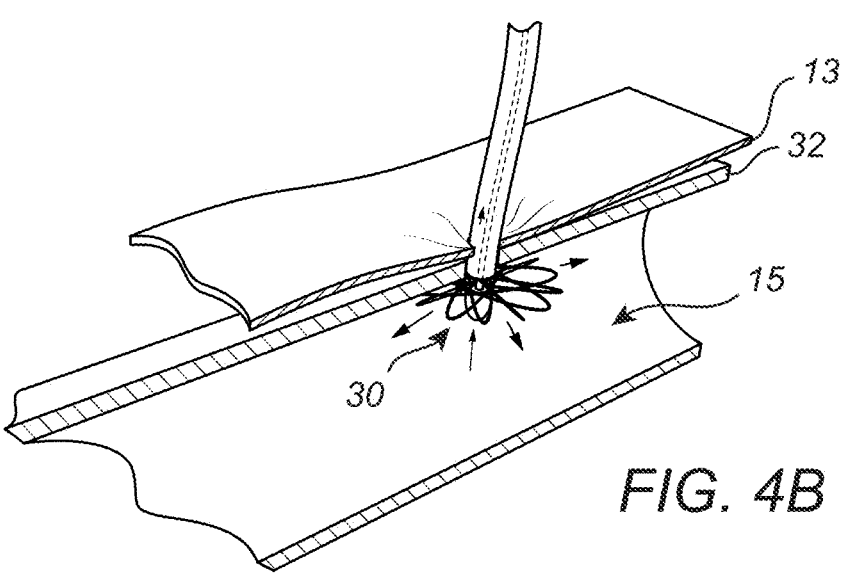

FIGS. 4A and 4B conceptually illustrate the operation of an anvil member exemplified as a deployable positioning feature 30. In FIG. 4A, deployable positioning feature 30 may be inserted through the wall 32 and into the interior volume of the blood vessel, such as the femoral artery 15. The deployable positioning feature 30 may be structured similar to an umbrella (using a mesh material), where the deployable positioning feature 30 in a radially collapsed form may be inserted into the artery 15. Once within the artery 15, with further reference to FIG. 4B, the deployable positioning feature 30 may be "unfolded" and radially expanded from the collapsed form such that a total surface area proximate to the longitudinal axis of the deployable positioning feature 30 is increased and thus may be retracted towards the interior wall of the artery 15. Accordingly, a reference point may be thereby established for further operation of the vascular closure device 10.

As discussed above, some undesirable peri-procedural back-bleeding may occur during use and deployment of vascular closure device embodiments discussed above as well as others discussed herein. Embodiments of vascular closure devices that include hemostatic functions discussed herein may be useful to prevent or reduce such peri-procedural back-bleeding from a patient's vessel during a vascular closure procedure. Such hemostatic functions may be achieved by using a self-expanding plug embodiment which exerts its sealing function from outside the vessel wall and typically not from the inside of the vessel. Such self-expanding plug embodiments may also restrict blood leakage from the access passage of the fascia layer 13 adjacent the vessel 15 as a vascular closure device is being deployed.

Figure 5:
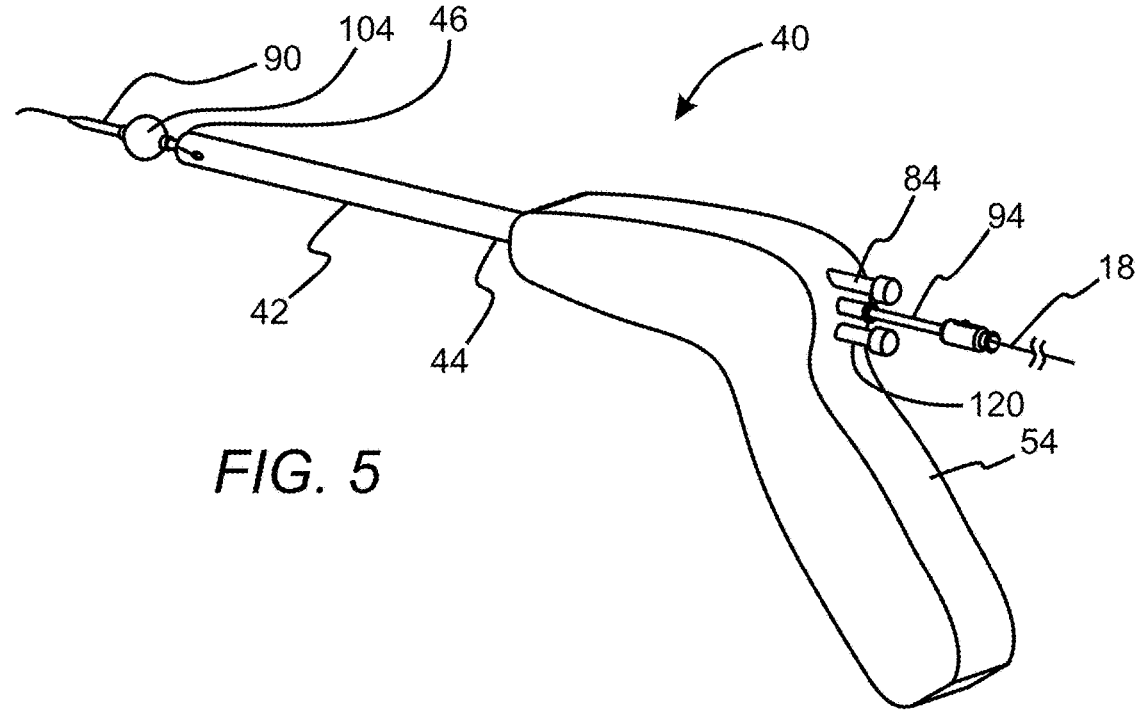
FIG. 5 is a perspective view of a vascular closure device embodiment.
Figure 6:
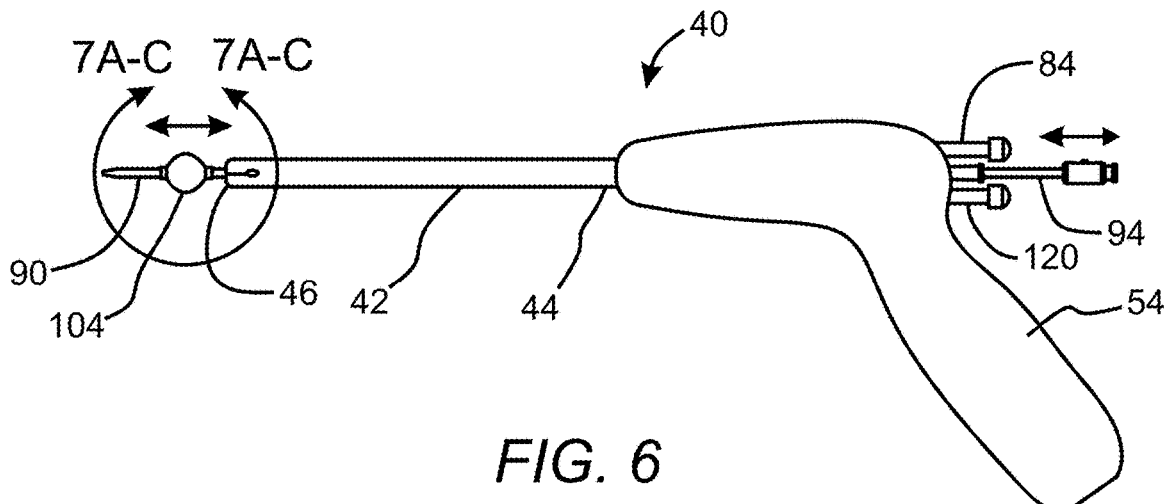
FIG. 6 is an elevation view of the vascular closure device embodiment of FIG. 5.

FIGS. 5-23 show embodiments of a vascular closure device 40 that includes hemostatic components and functions. As shown in FIGS. 5-6, the vascular closure device embodiment 40 may have an outer housing 42 with an elongate configuration with an axial length greater than a transverse dimension thereof, a proximal end 44, a distal end 46, an inner lumen 48 extending from the proximal end 44 to the distal end 46, and a distal section 50. The vascular closure device embodiment 40 may also include a handle 54 secured to the proximal end 44 of the outer housing 42. The handle 54 may include a variety of controls which may be used to close the access hole 56 in a patient's vessel 15 as well as actuate the hemostatic functions of the vascular closure device 40.

The vascular closure device 40 may also include a plurality of anchor deployers 58 which are slidably disposed within axial lumens 62 of the outer housing 42 adjacent each other at the distal section 50 of the outer housing 42 as shown in FIGS. 9A-11. The plurality of anchor deployers 58 may be configured to extend and spread from the distal section 50 of the outer housing 42. Each of the anchor deployers 58 may include a deployment rod 64 which is slidably disposed relative to the outer housing 42 within one of the axial lumens 62 and which includes an elongate resilient configuration. A distal end 66 of each deployment rod 64 may be configured to extend from the distal section 50 of the outer housing 42 to a position that is distal of the distal end 46 of the outer housing 42 in some cases.

Figure 10:
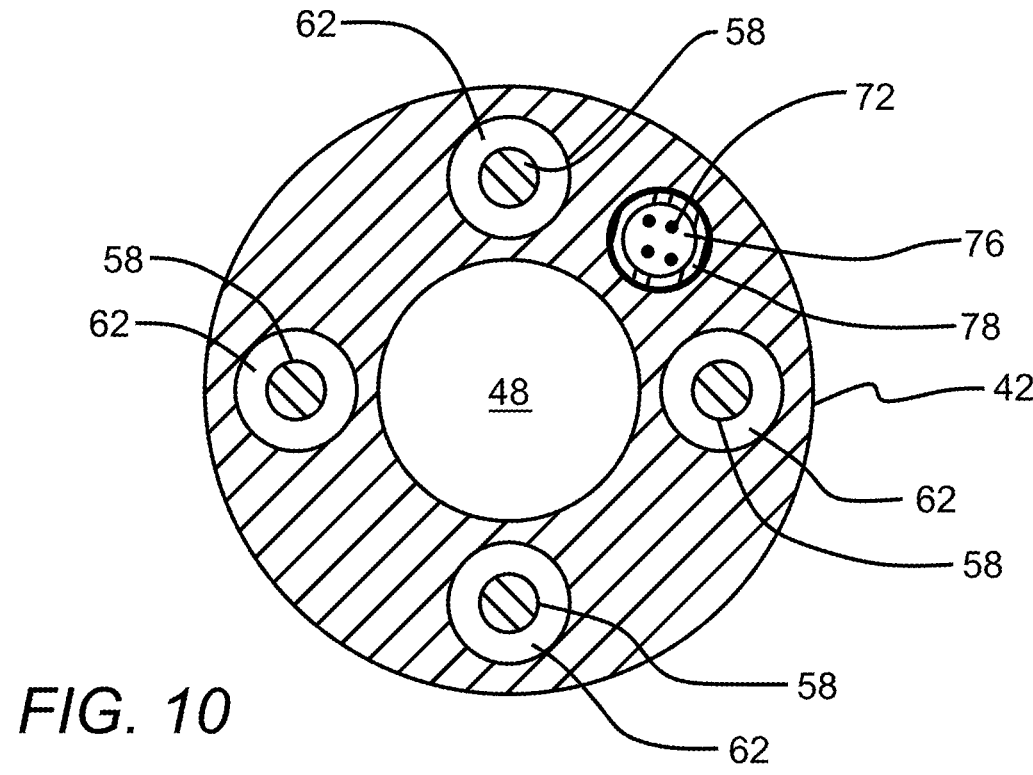
FIG. 10 is a transverse cross section view of the outer housing taken along lines 10-10 of FIG. 8.
Figure 11:
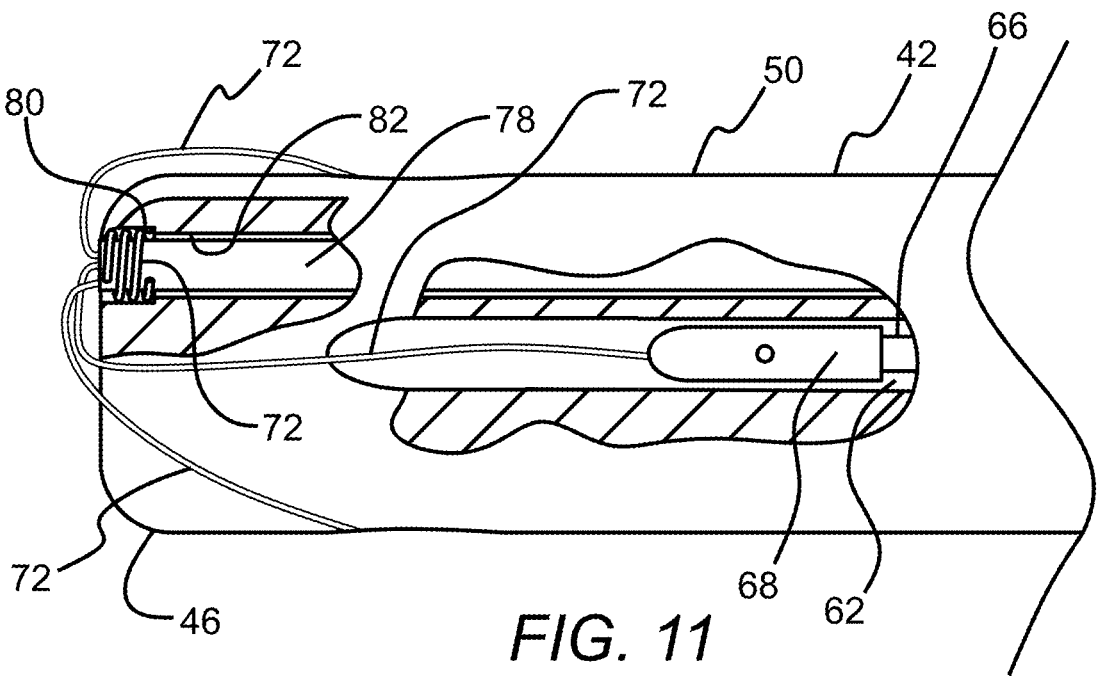
FIG. 11 is an enlarged view in partial section of the outer housing of the vascular closure device of FIG. 8 indicated by the encircled portion 11-11 of FIG. 8.
Figure 29:
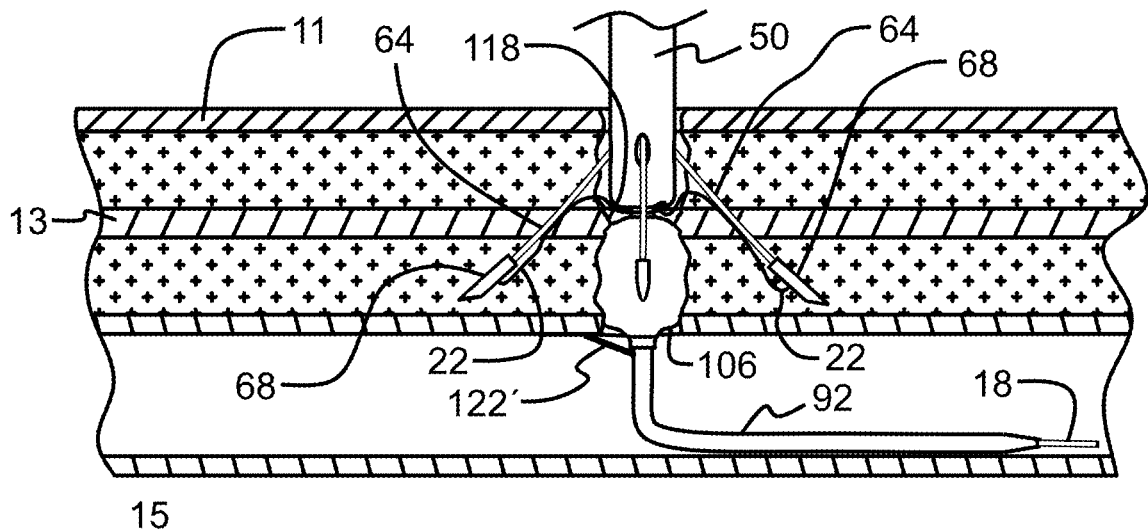
Figure 31:
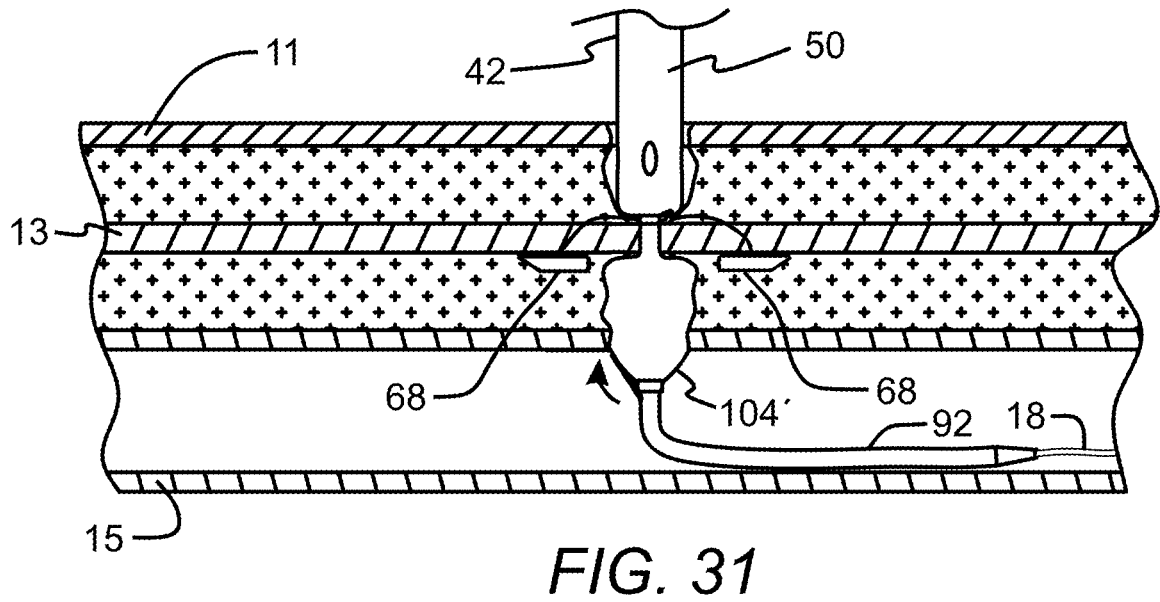

Each of the anchor deployers 58 may also include an anchor 68 which is removably secured to the distal end 66 of the deployment rod 64 thereof. The anchor 68 may be configured to penetrate tissue such as a fascia tissue layer 13 or the like in a distal direction as shown in FIG. 29. Thereafter, each anchor 68 may be released from the distal end 66 of the deployment rod 64 and rotated or toggled so as to prevent withdrawal of the anchor 68 back through the hole created by penetration of the tissue layer 13 by the anchor 68 as shown in FIG. 31. Each anchor deployer 58 may also include a filament 72, such as a suture, that includes a distal end 74 which is secured to the anchor 68 of the anchor deployer 58 and which is slidably disposed within the outer housing 42. Each filament 72 may be used to retract the respective anchor 68 to which it is secured and a tissue portion of the tissue layer 13 secured to the anchor 68 back towards the distal end of the outer housing 42. In some instances, each of a plurality of the filaments 72 of respective anchor deployers 58 may be routed through an inner lumen 76 of a filament tube 78 that is axially translatable within a lumen 82 of the outer housing as shown in FIGS. 10 and 11.

For some embodiments, a deployment rod pusher 84, as shown in FIG. 5, may be operatively coupled to each deployment rod 64 of each of the plurality of anchor deployers 58. In some cases, such a deployment rod pusher 84 may be operatively coupled to a proximal end of each deployment rod 64 of the plurality of anchor deployers 58 and configured to extend each deployment rod 64 in a distal direction upon actuation. For some embodiments, the deployment rod pusher 84 may optionally be spring loaded and biased towards a retracted position.

In some cases, the vascular closure device 40 includes a tissue grip which is deployable from the distal end 46 or distal section 50 generally of the outer housing 42. The tissue grip may be configured to secure tissue portions in fixed relation to each other once they have been drawn together by the anchors 68 and associated filaments 72 of the anchor deployers 58. In some cases, embodiments of the tissue grip may be disposed on the distal end 46 of the outer housing 42 around each filament 72 of the plurality of anchor deployers 58. Such a tissue grip embodiment may be configured to compress and secure each of the filaments 72 relative to each other once the tissue grip is deployed from the distal end 46 of the outer housing 42 as shown in the deployment sequence of FIGS. 34 and 35.

Figure 34:
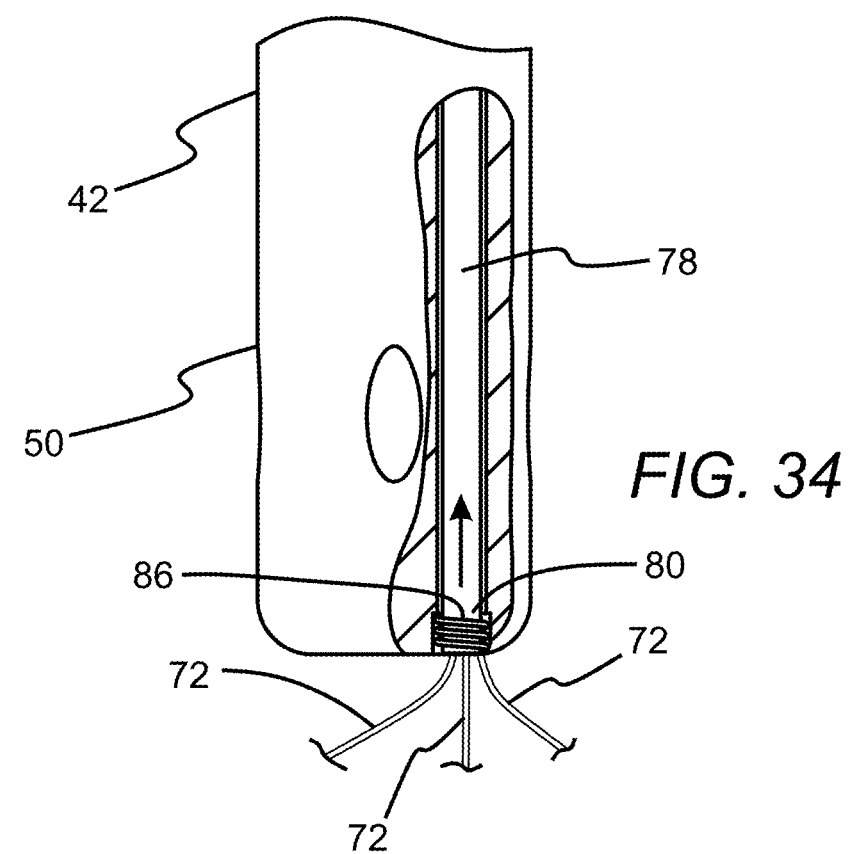
Figure 35:
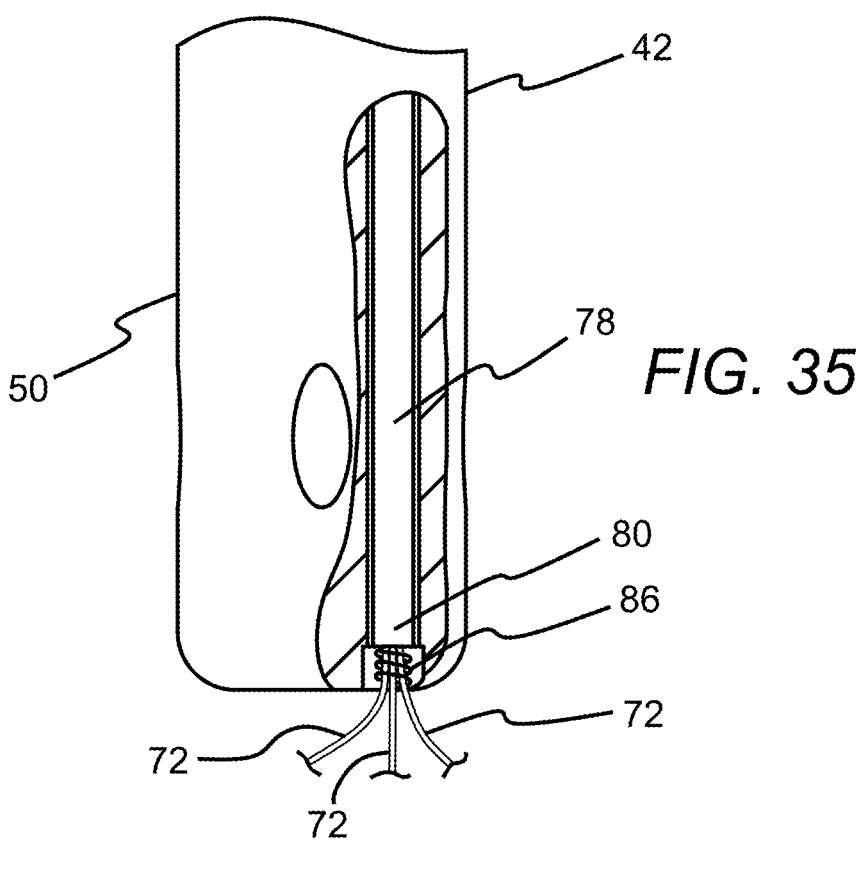

In some cases, such a tissue grip embodiment may include a lock ring 86 disposed about the filament 72 of each of the plurality of anchor deployers 58. The lock ring 86 may be configured as a self-retracting coil with a central lumen which is sized to allow movement of each filament 72 of the plurality of anchor deployers 58 while the self-retracting coil 86 is in an expanded state as shown in FIG. 34. The self-retracting coil embodiment 86 may also have an interior surface of the central lumen thereof that is configured to compress and secure each filament 72 of the plurality of anchor deployers 58 relative to each other when in a retracted state as shown in FIG. 35. In some other instances, embodiments of the tissue grip may include a tissue adhesive that may be dispensed from an outlet port (not shown) at the distal end 46 of the outer housing 42 onto tissue portions which have been gathered by the retraction of anchors 68 and respective filaments 72 of the vascular closure device 40. For some embodiments, such a tissue adhesive may include cyanoacrylate adhesive or the like.

Regarding peri-procedure hemostatic functions, the vascular closure device 40 may also include an inner hemostatic assembly 90 that has an elongate shaft 92 with an axial length greater than a transverse dimension thereof, a proximal end 94, a distal end 96 and a distal section 98 that is axially slidable within the inner lumen 48 of the outer housing 42. In some cases, a majority of an axial length of the inner hemostatic assembly 90 may be axially slidable within the inner lumen 48 of the outer housing 42 of the vascular closure device 40. The axial length of the elongate shaft 92 may also be longer than an axial length of the outer housing 42 in some cases such that the proximal end 94 and distal end 96 of the elongate shaft 92 may simultaneously extend axially from the inner lumen 48 of the outer housing 42 while the inner hemostatic assembly 90 is disposed within the inner lumen 48. The elongate shaft 92 of the inner hemostatic assembly 90 may also have a guidewire lumen 102 disposed within an outer surface of the elongate shaft 92 which extends from the proximal end 94 to the distal end 96 thereof.

Figures 7A, 7B, 7C:
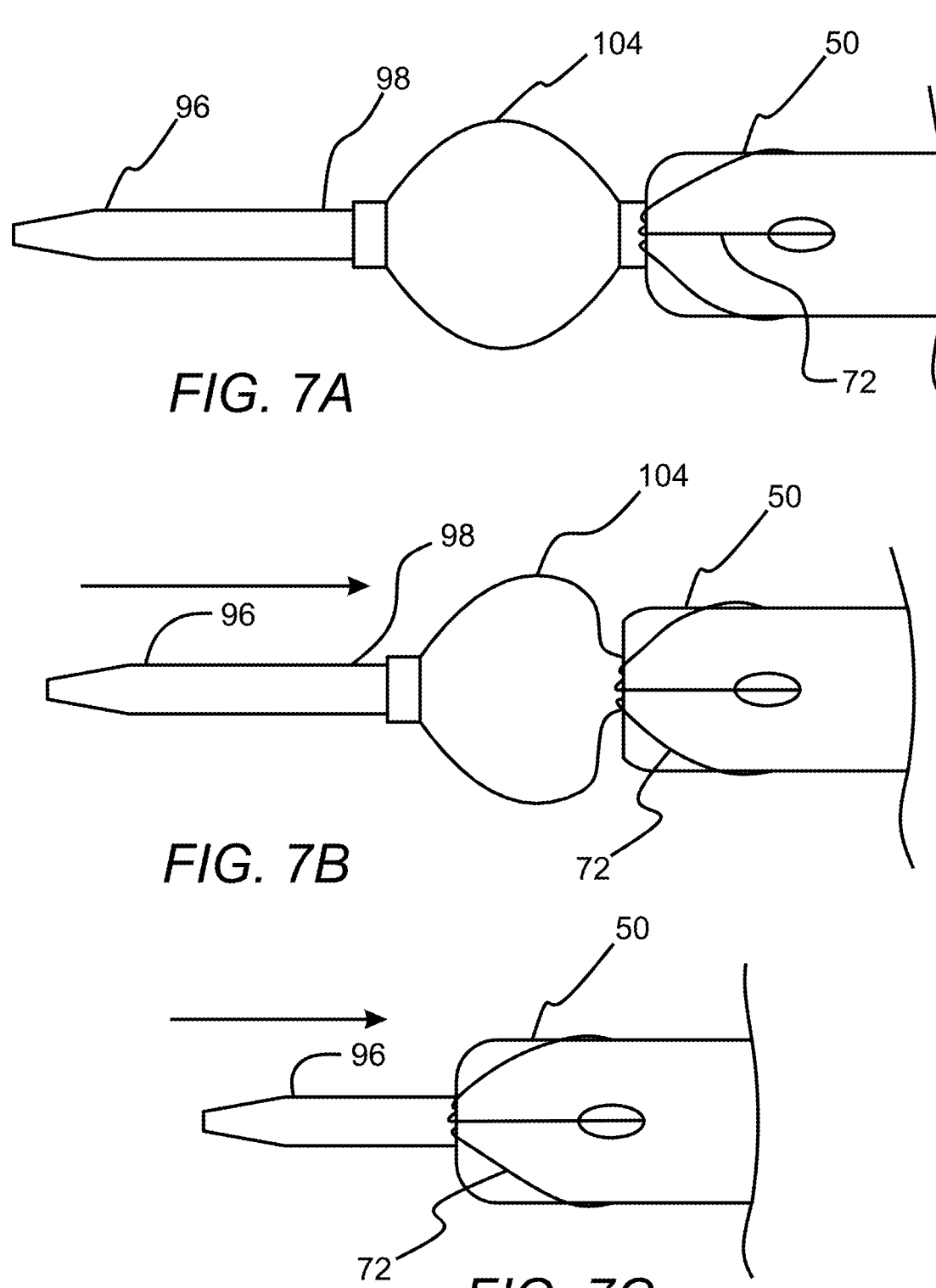
FIGS. 7A-7C are enlarged views of a distal section of an outer housing of the vascular closure device embodiment of FIG. 5 indicating axial movement between an inner hemostatic assembly of the vascular closure device and the outer housing thereof.
Figure 8:
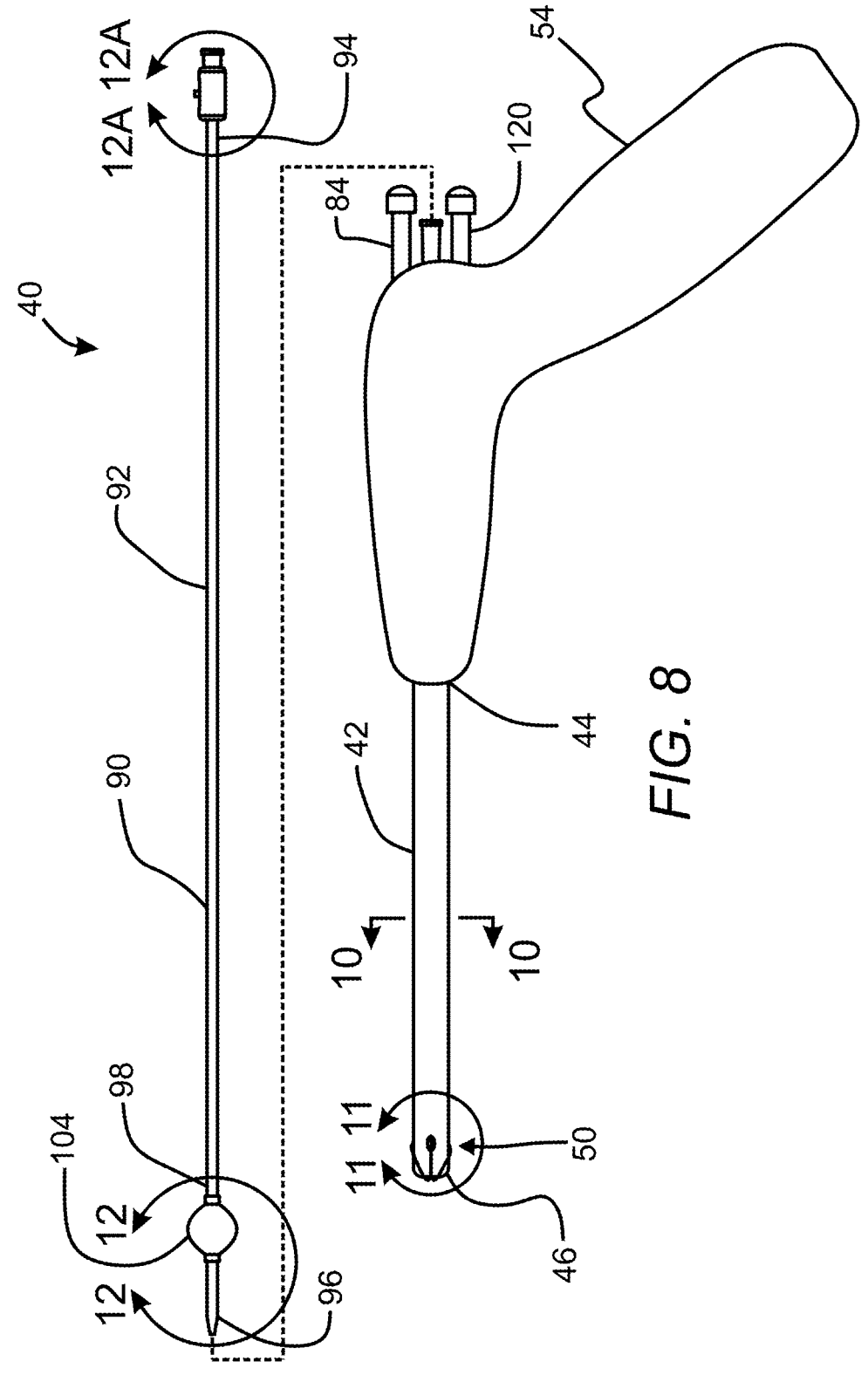
FIG. 8 is an elevation view of the vascular closure device embodiment of FIG. 5 with the inner hemostatic assembly axially withdrawn from the outer housing.
Figure 9:
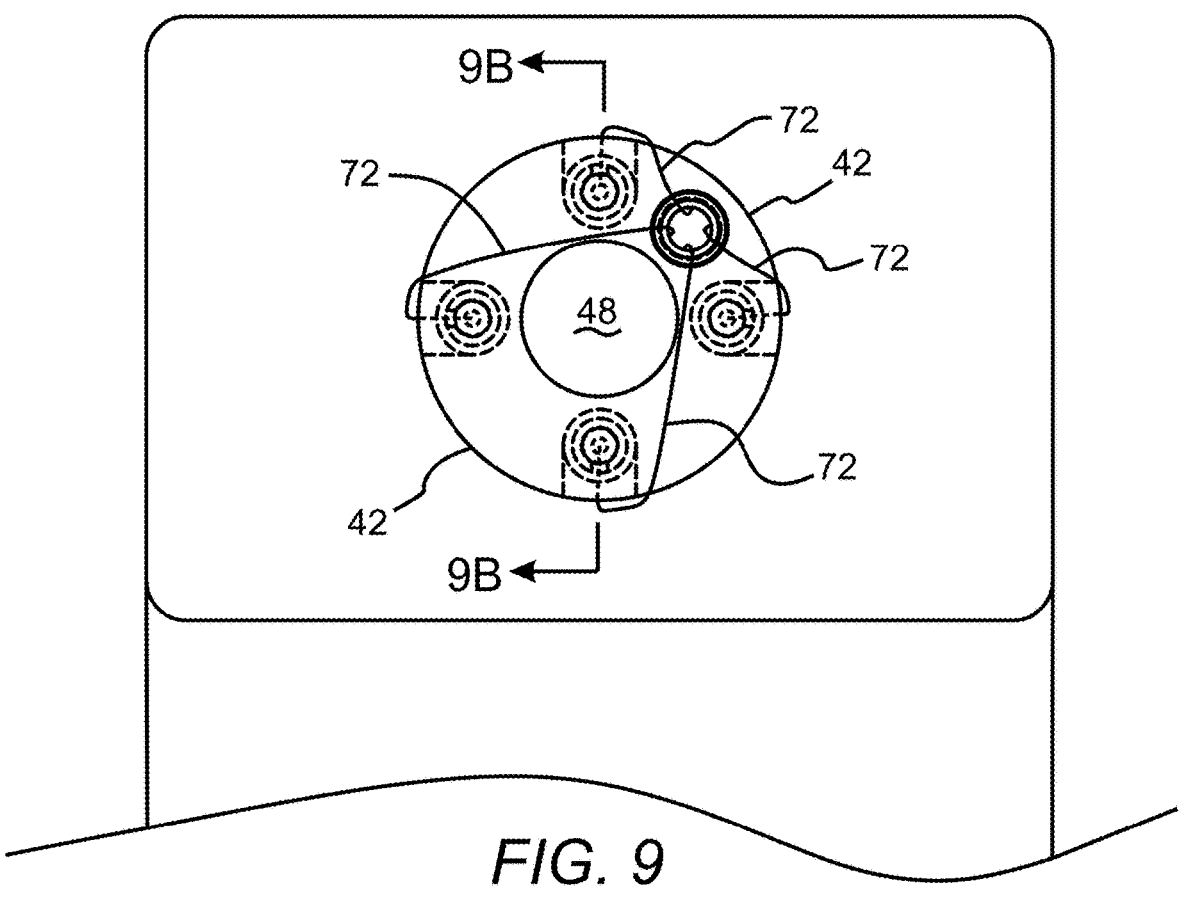
FIG. 9 is a front view of the vascular closure device embodiment of FIG. 5.
Figure 9A:
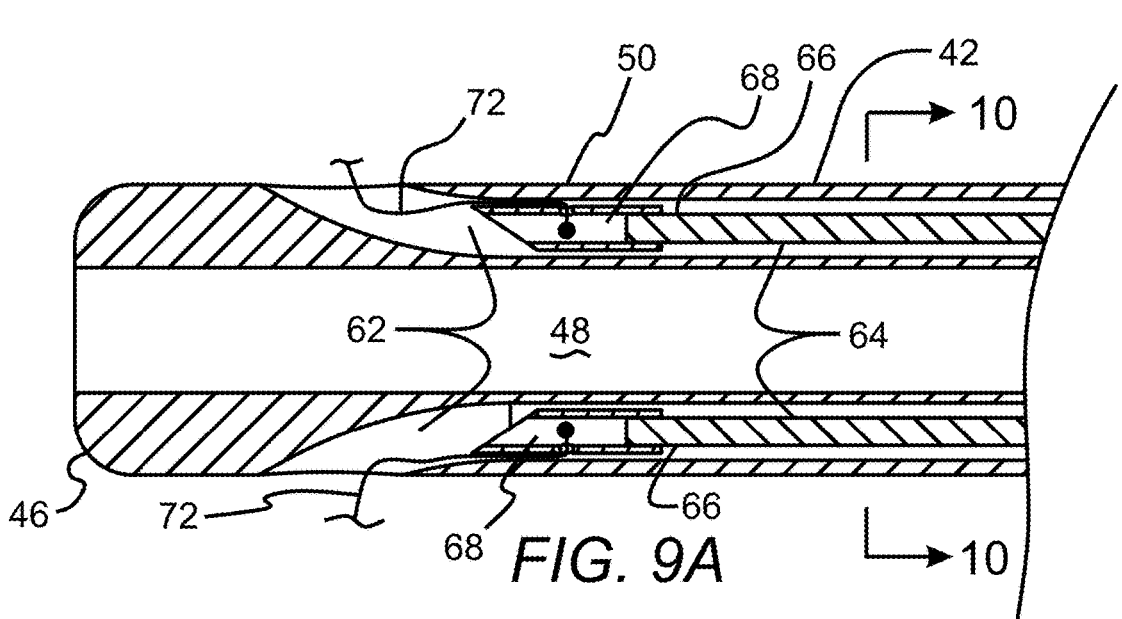
FIG. 9A is an enlarged view in longitudinal section of a distal section of the outer housing of the vascular closure device of FIG. 8.

The inner hemostatic assembly 90 also includes a self-expanding plug 104 which is disposed on the distal section 98 of the elongate shaft 92 proximal of the distal end 96 of the elongate shaft 92. The self-expanding plug 104 may have an outer profile that is configured to self-expand from a compressed state to an expanded state. In the compressed state, the self-expanding plug 104 may be sized to fit and axially slide within the inner lumen 48 of the outer housing 42. As shown in FIGS. 7A-7C, the self-expanding plug may be proximally withdrawn into the inner lumen 48 by axially translating the elongate shaft 92 in a proximal direction. In the expanded state, the self-expanding plug 104 may have an outer transverse dimension which is larger than an outer transverse dimension of the elongate shaft 92 and which may be sized to reduce or eliminate leakage of blood from an access hole 106 in the vessel 15. In some cases, a major outer transverse dimension of the self-expanding plug 104 in an expanded state may be about 5 mm to about 20 mm, more specifically, about 8 mm to about 15 mm. For some embodiments, a profile of an outside surface of the self-expanding plug 104 may have a generally spherical or ovoid shape or any other suitable shape.

In some cases, the self-expanding plug 104 may include a plurality of elongate beams 108 which may have a smoothly curved shape, which are secured to the elongate shaft 92 in a generally axially oriented direction and which are resilient and elastic to allow for compression and self-expansion of the self-expanding plug 104. The beams 108 may be covered by a bag 112 of thin flexible material that is typically close fitted to an outside surface of the beams 108 when the beams 108 are in an expanded state. The thin flexible material of the bag 112 may be configured to form a balloon shaped enclosure disposed about the beams 108 to prevent a passage of blood through a layer of the bag 112. As discussed above, an outer profile of the bag 112 may have a generally spherical or ovoid shape when the self-expanding plug 104 is in an expanded or partially expanded state. Some bag embodiments 112 may be vented with one or more ports (not shown) in fluid communication between an inside volume of the bag 112 and the space surrounding the bag 112 in order to accommodate fluctuations in the internal volume of the bag embodiments 112 during expansion and compression of the bag embodiments 112.

Figure 13:
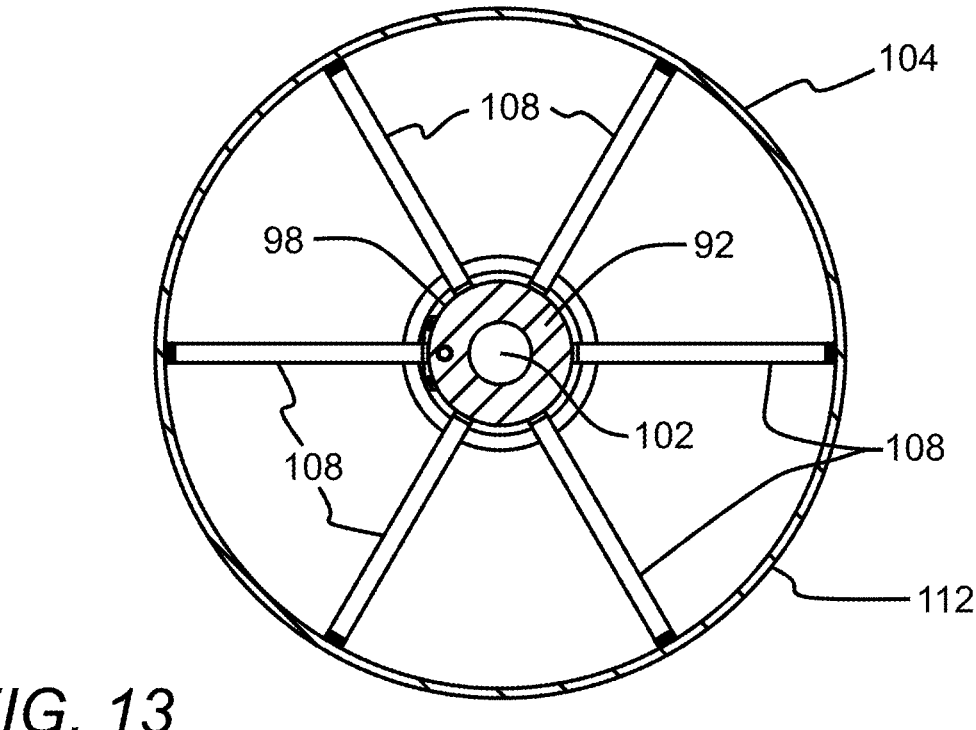
FIG. 13 is a transverse section view of the inner hemostatic assembly and self-expanding plug thereof taken along lines 13-13 of FIG. 12.
Figures 14, 15:
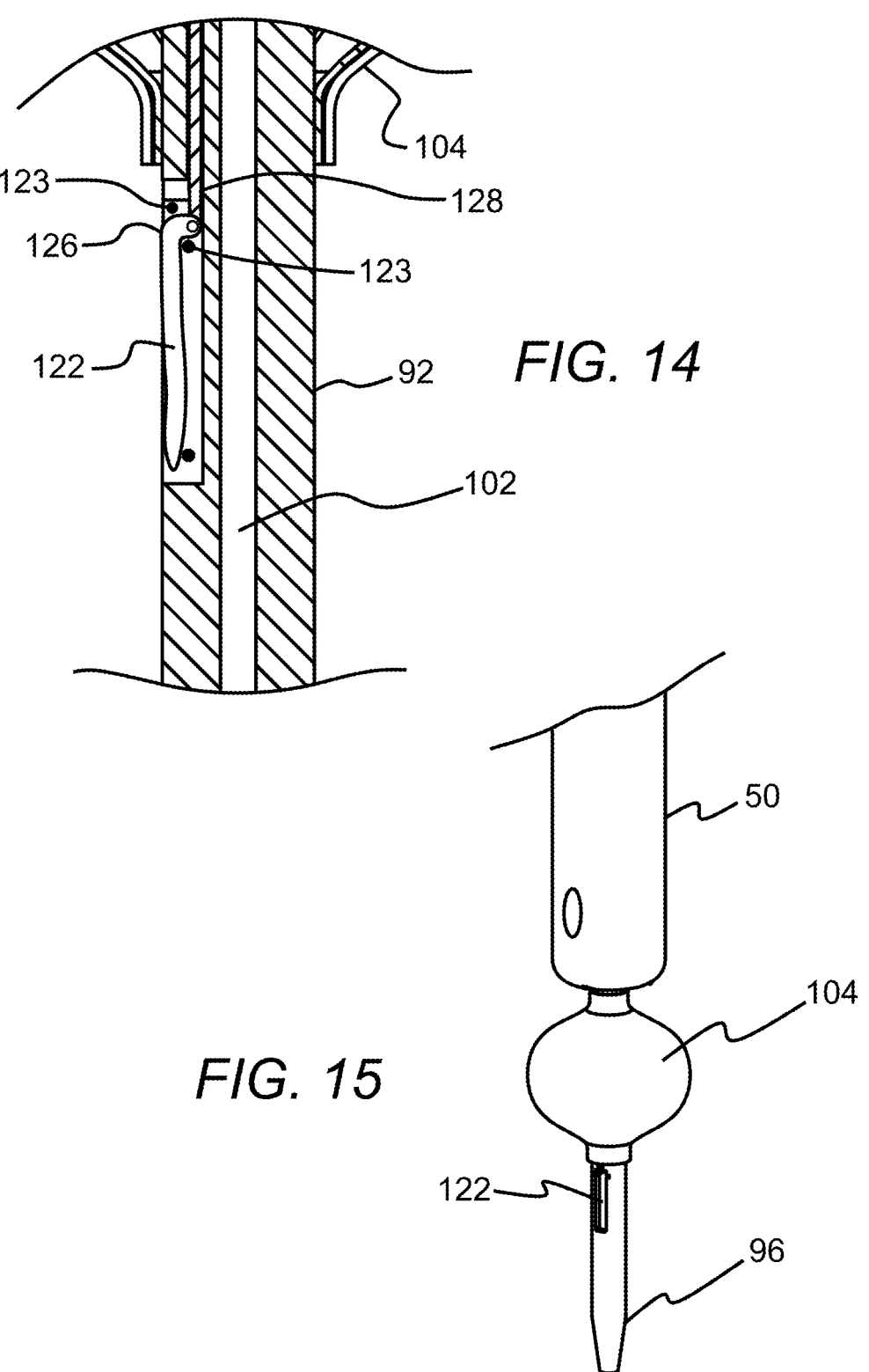
FIG. 14 is an enlarged view in longitudinal section of a distal section of the inner hemostatic assembly indicated by the encircled portion 14-14 of FIG. 12 shown with a foot thereof in a retracted position.
FIG. 15 is a perspective view of a distal section of the inner hemostatic assembly of FIG. 14 shown with the foot in the retracted position.
Figures 16, 17:
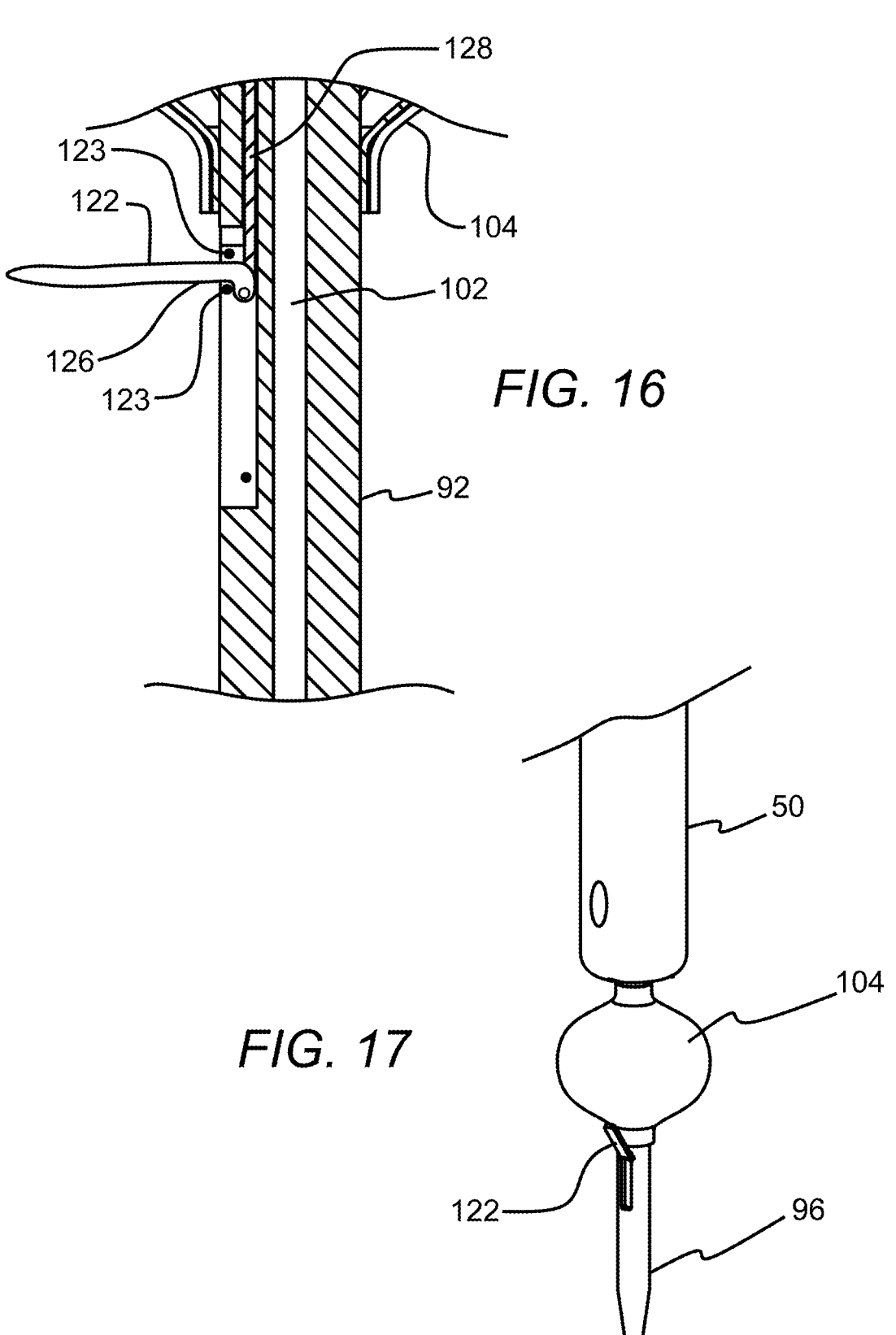
FIG. 16 is an enlarged view in longitudinal section of a distal section of the inner hemostatic assembly of FIG. 14 shown with the foot thereof in a deployed position.
FIG. 17 is a perspective view of the distal section of the inner hemostatic assembly of FIG. 16 shown with the foot in the deployed position.

Instead of using a bag 112 made from a layer of flexible material disposed over the beams 108, the beams 108 may also be attached side-by-side to each other with a structure that has a layer of soft flexible material secured to and extending between side edges of adjacent beams 108 with a type of "beam-soft material-beam-soft material" repeating structure (not shown) in some embodiments. In some embodiments, beams 108 alone without a bag may be arranged and/or constructed in a way that they leave a minimum gap between the individual beams 108 when they are expanded to the expanded state. For some embodiments, the self-expanding plug 104 may optionally be made from a resilient and elastic foam material that does not require the use of a composite structure with beams 108 and bag 112. FIG. 13 shows a self-expanding plug embodiment 104 in an expanded state in the mid-portion and shows a configuration where the beams 108 push out the surrounding bag 112. FIG. 13 shows a self-expanding plug embodiment 104 having a total of six beams 108, however, but more or less beams 108 may also be used. For example, some self-expanding plug embodiments may have about 4 beams 108 to about 30 beams 108, more specifically, about 8 beams 108 to about 12 beams 108.

The elongate beams 108 may have a curved profile with an apex of curvature that may be disposed at an axial position on the beams 108 that is approximately at the midpoint thereof. The apex of curvature also extends radially outward from an outer surface of the elongate shaft 92. The pre-curved wires or beams 108 may be self-expandable to fill up space adjacent the vessel wall 32, such as the fascia 13 and the interstitial tissue 17 between the level of the fascia 13 and the vessel wall 32. Some embodiments of the self-expanding plug 104 may include supporting wires or beams 108 that are molded to the elongate shaft 92 of inner hemostatic assembly 90 at one distal and one proximal end on the beams 108. The pre-curved beams (or wires) 108 on the inside of the bag 112 may attached to the self-expanding plug 104 on just one end of the beams 108. In some instances, the beams 108 may be attached at a distal end 114 thereof but optionally not attached at a proximal end 116 thereof which allows the proximal ends 116 of the beams (wires) 108 to slide and compress in relation to the elongate shaft 92 which results from the bag 112 expanding and contracting. The pre-curved wire or beam embodiments 108 may include resilient elastic materials such as spring steel, superelastic materials such as nickel titanium alloys such as nitinol or various polymers in some cases. The material of the bag 112 may include soft synthetic or biologic material used for example in standard balloons, such as nylon, polyurethane, polytetrafluoroethylene (PTFE) or the like.

Some self-expanding plug embodiments 104 may be easily compressible to a relatively small diameter by application of an outside compressive force so that the self-expanding plug embodiments 104 may easily slip through the access hole 106 in the vessel wall 32 and access passage 118 of the fascia 13 without interfering with the normal use of other components of vascular closure device embodiments 40 and without complicating the maneuvers of the vascular closure device 40 which may be integrated with self-expanding plug 104. Some self-expanding plug embodiments 104 may be configured to fill up the access hole 106 in the vessel wall 32 and the access passage 118 of the fascia 13 in front of the vessel wall 32. Some wire or beam embodiments 108 of the self-expanding plug 104 may, in some cases, have enough resistance to compression to resist the blood pressure within a vessel 15 (without collapsing) but not so much force as to cause non-reversible change of the anatomy of the vessel wall 32 and the fascia 13. In some instances, avoiding a non-reversible change of the anatomy might include avoiding increasing the size of the access hole 106, access passage 118 or the like in a permanent manner such as by tearing the tissue adjacent the access hole 106 or access passage 118. In some instances, the self-expanding plug 104 in a compressed state or partially compressed state may be configured to exert an outward radial pressure that is equal to about a systolic blood pressure of the patient to about two times the systolic blood pressure of the patient. In some cases, embodiments of the self-expanding plug 104 in a compressed state may be configured to exert an outward radial pressure equal of about 2 psi to about 4 psi.

Figure 28:
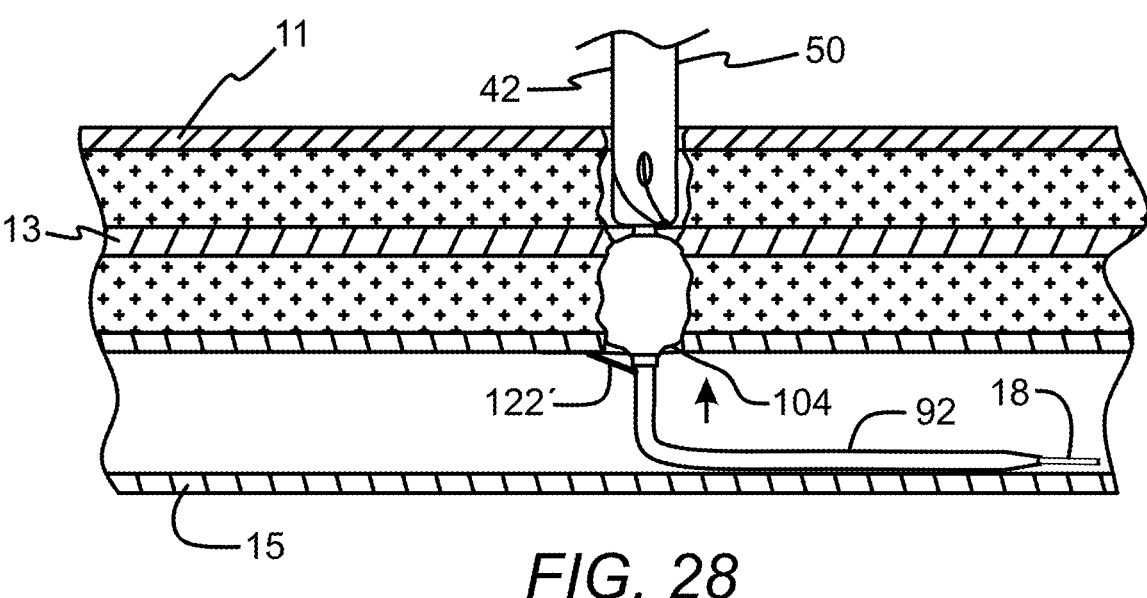

Some embodiments of the inner hemostatic assembly 90 may include a lateral surface, which may be configured in the form of a foot 122 in some cases. As shown in FIGS. 14-17, the foot embodiment 122 may be configured to extend radially outward from the distal section 98 of the elongate shaft 92 distal of the self-expanding plug 104 while the foot 122 is disposed within an inner lumen of the blood vessel 15 or at any other suitable axial position. The foot 122 may extend laterally and axially outward so as to extend axially outward of an outer surface of the elongate shaft 92 and engage an inner surface 124 of the blood vessel 15 to prevent further proximal retraction of the elongate shaft 92 once so engaged. Such a laterally extended foot 122 may be used to provide a reference point between relative axial positions of the wall 32 of the blood vessel 15 and the self-expanding plug 104 as shown in FIG. 28. In some cases, the foot 122 may be hinged by pivot pins 123 or the like with an inner end 126 pivotally secured to the elongate shaft 92 by the pivot pins 123. For some embodiments, the pivot pins 123 may include rigid high strength pins with an elongate shape which are secured to the outer housing 42. Some embodiments of the foot 122 may have a length of about 2 mm to about 10 mm.

The foot 122 which may be used for providing a reference surface for axial positioning of the self-expanding plug 104 may be located on the elongate shaft 92 so that the foot 122 extends from the elongate shaft 92 at a position just distal of the position where the distal end of self-expanding plug 104 is molded to the elongate shaft 92. That is, some embodiments of the foot 122 may be configured to hinge and extend from a position on the elongate shaft that is just distal of the distal end of the self-expanding plug 104. In some cases, the foot 122 may hinge and extend from a position that is up to about 5 mm distal of the distal end of the self-expanding plug 104.

Figure 23:
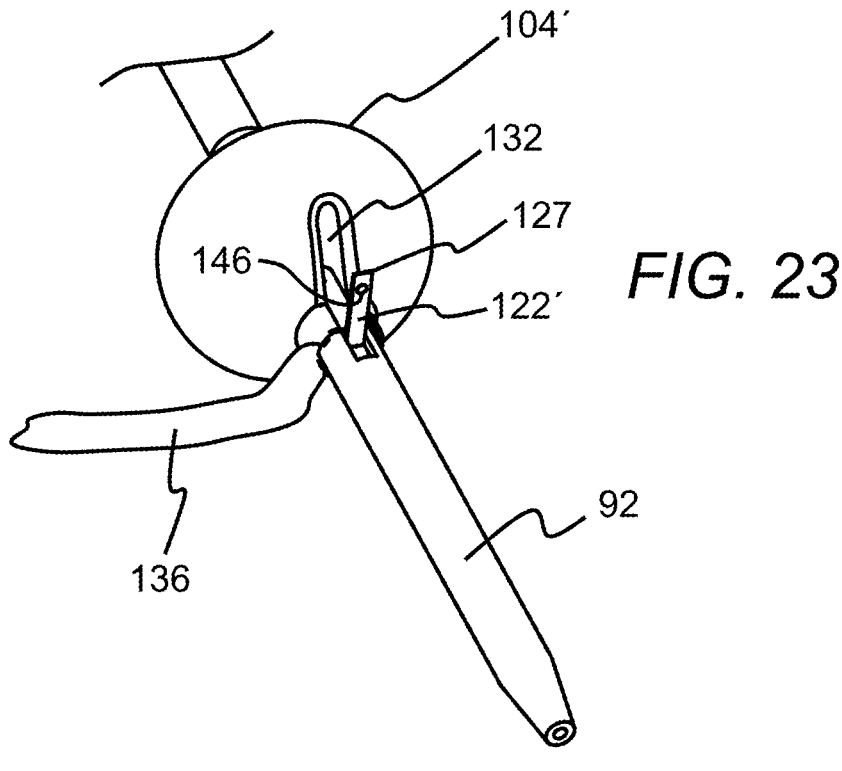
FIG. 23 is a perspective view of the distal section of the inner hemostatic assembly of FIG. 19 shown with the self-expanding plug in an expanded state and with the foot in the deployed position.

The foot 122 may be folded out in different ways so as not to interfere with the self-expanding plug 104. The foot 122 may be deployed by virtue of suitable proximal or distal movement of a rod 128 that is coupled between the foot 122 and a foot actuator 134 as shown in in FIG. 12A. In some instances, the foot actuator 134 may be disposed at the proximal end 94 of the elongate shaft 92 of the inner hemostatic assembly 90 and may be operatively coupled to such hinged foot embodiments. The foot embodiment 122 shown in FIGS. 14-17 is disposed distally of the self-expanding plug embodiment 104 shown therein and thus outward deployment of the foot 122 does not interfere with the self-expanding plug embodiment 104 shown. FIG. 23 shows an embodiment of the inner hemostatic assembly 90 wherein the foot 122 may be folded out, for example, through a groove 132 in the self-expanding plug embodiment 104' so as not to interfere with the self-expanding plug embodiment 104 during deployment.

Referring to FIGS. 18-23, some embodiments of the inner hemostatic assembly 90 may include a sock constraint 136 disposed over and constraining the self-expanding plug 104' in a constrained state prior to deployment. Such a sock constraint 136 may be released from the constrained state by removal of a restraining member such as a thread 138 which may be secured to opposed edges 142 of the sock constraint 136 and which may be severed to release the sock constraint 136 from the constrained state. In some cases, the sock constraint 136 may be removed when the vascular closure device 40 is at the intended position relative to the patient's vessel 15 as shown, for example, in the deployment sequence of FIGS. 37-39. The optional sock constraint 136 that surrounds the self-expanding plug 104' to keep it in a collapsed state may make it easier to maneuver the vascular closure device 40 and particularly the inner hemostatic assembly 90 thereof prior to release of the sock constraint 136 in some instances.

The sock constraint 136 may be molded and secured to the self-expanding plug 104' at the distal end thereof and each circumferential edge 142 of the sock constraint 136 may be joined together by the thread 138 that runs through loops 144 secured to respective circumferential edges 142. The thread 138 and loops 144 may have a configuration similar to that of a shoestring in some cases. Each end of the thread 138 may be attached to the sock constraint 136 at two points, proximally and distally. At one position the thread 138 may extend through a hole 146 which has a sharpened edge in the foot 122' in a position where the foot 122' is not hinged, such as at the outer end of the foot 122'. The sock constraint 136 may include any suitable material that is used in covered stents (stentgrafts) and the thread 138 of any suitable non-elastic material, such as materials used for surgical sutures or the like. In some cases, the sock constraint 136 may be made from biocompatible polymers such as nylon, polytetrafluoroethylene, including expanded polytetrafluoroethylene, polyurethane or the like.

Figure 18:
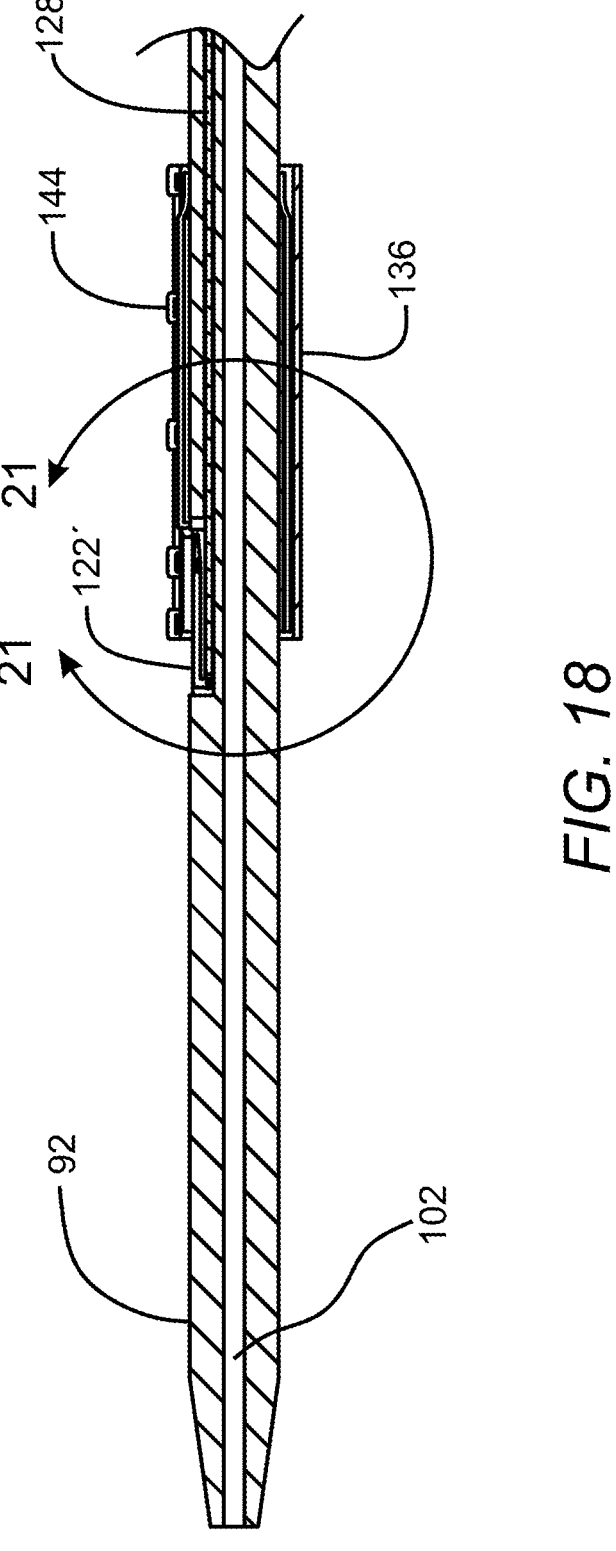
FIG. 18 is an enlarged view in longitudinal section of a distal section of an inner hemostatic assembly embodiment that includes a releasable sock constraint disposed over and constraining a self-expanding plug thereof and a foot disposed in a retracted position.
Figure 19:
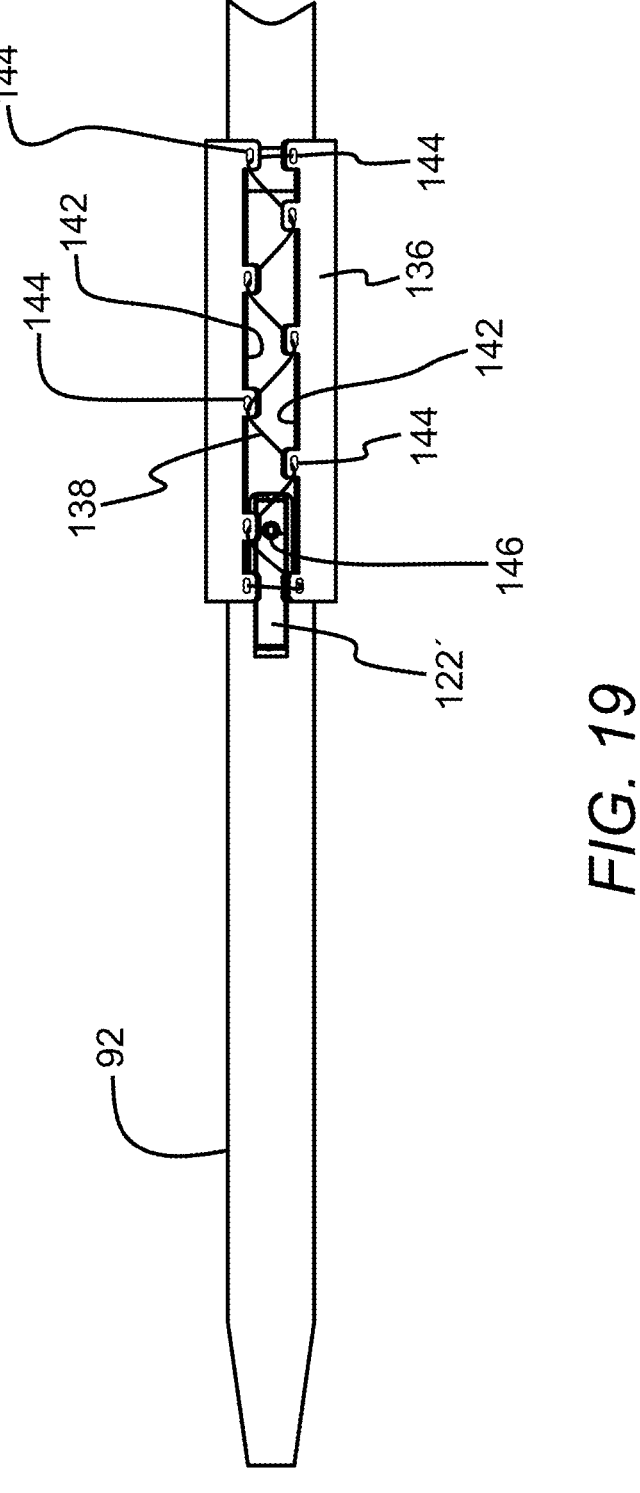
FIG. 19 is a top view of the distal section of the inner hemostatic assembly of FIG. 18.
Figure 20:
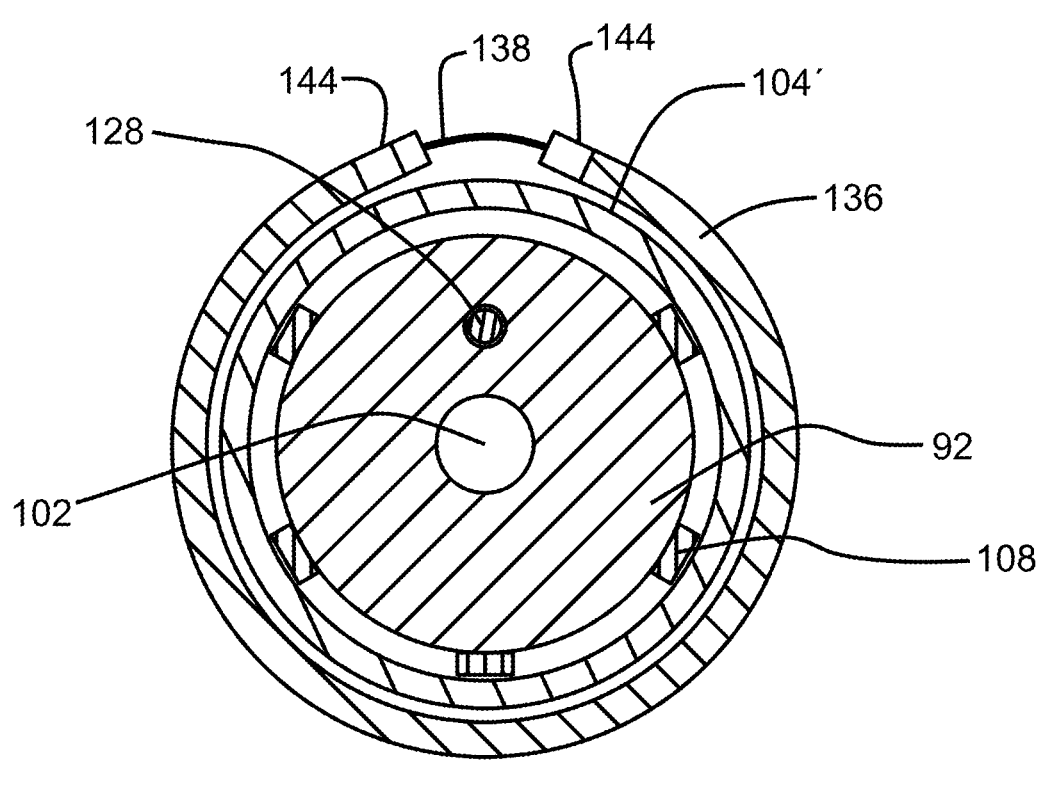
FIG. 20 is a transverse cross section view of the distal section of the inner hemostatic assembly of FIG. 18 taken along lines 20-20 of FIG. 18.
Figure 21:
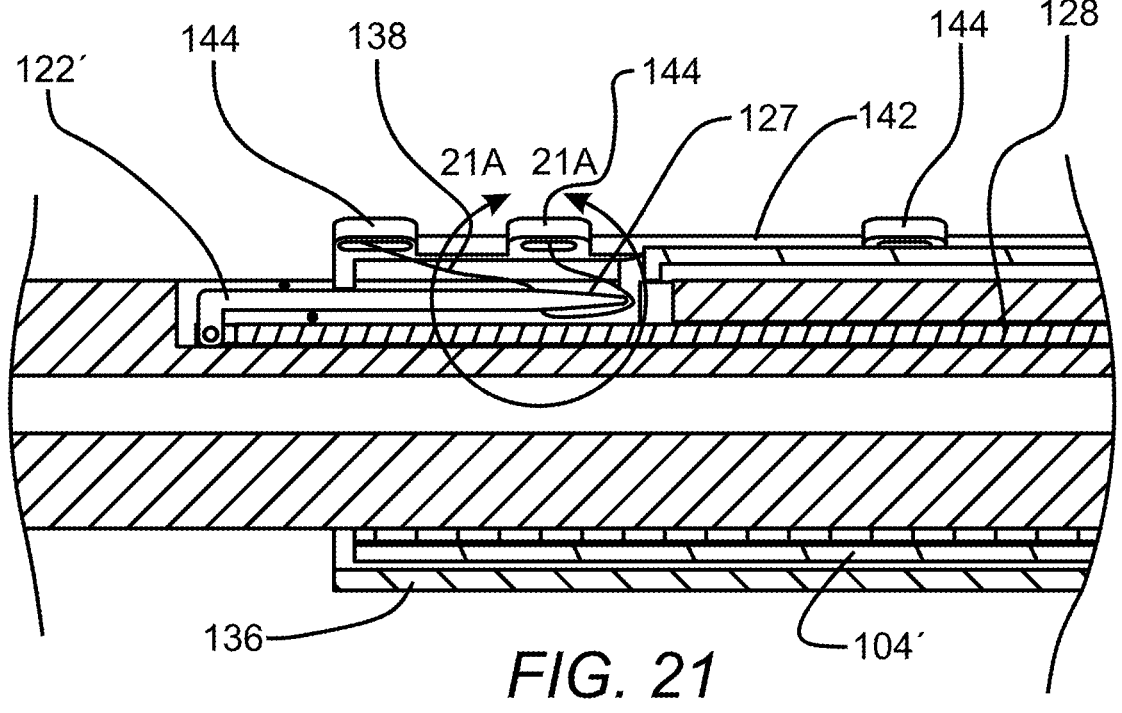
FIG. 21 is an enlarged view of the distal section of the inner hemostatic assembly of FIG. 18 indicated by the encircled portion 21-21 of FIG. 18 shown with the sock constraint constraining the self-expanding plug and with the foot in a retracted position.
Figures 21A, 22:
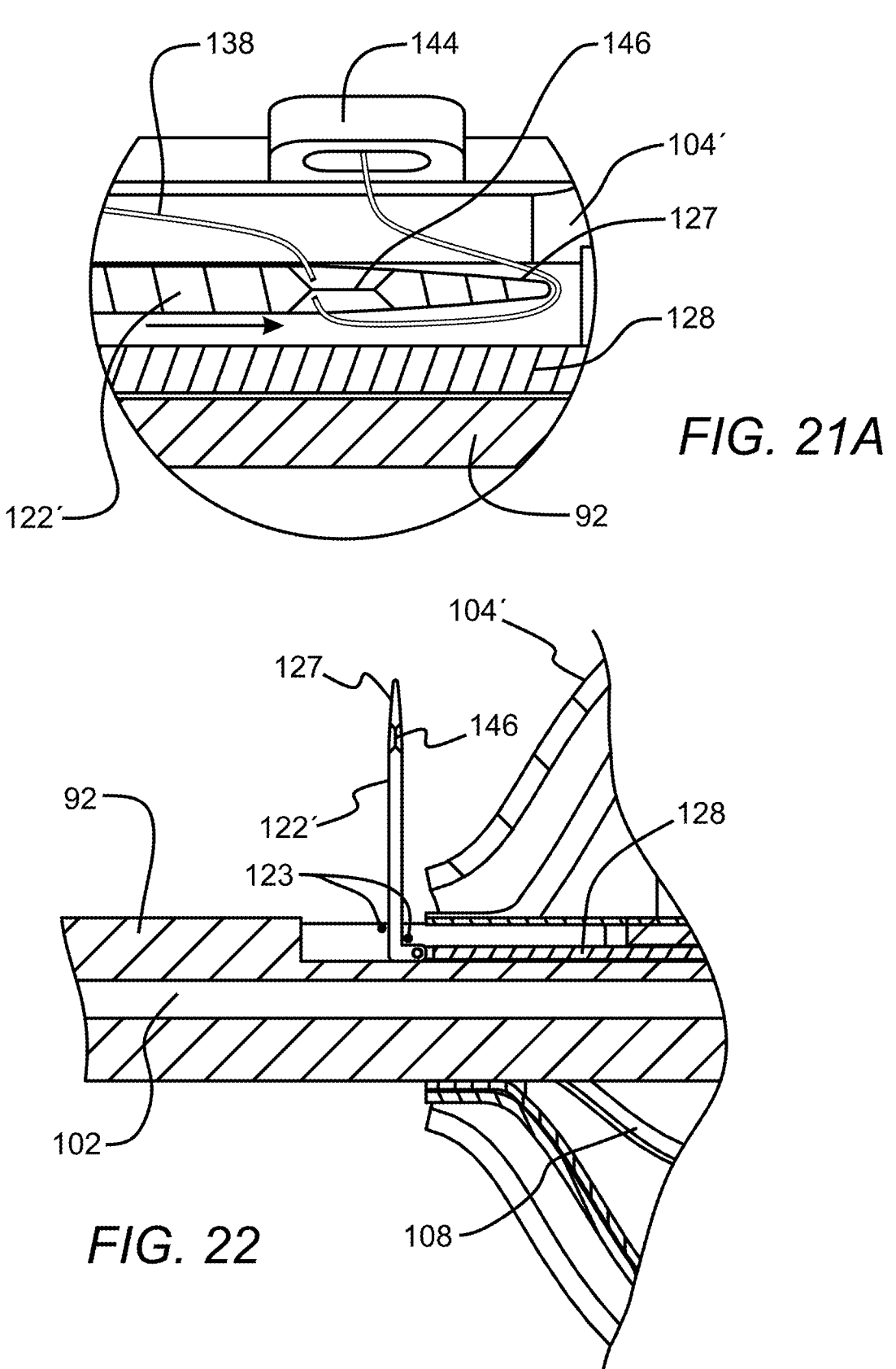
FIG. 21A is an enlarged view of the encircled portion 21A-21A of FIG. 21.
FIG. 22 is an enlarged view of the distal section of the inner hemostatic assembly of FIG. 18 indicated by the encircled portion 21-21 of FIG. 18 shown with the sock constraint in a released state no longer constraining the self-expanding plug and with the foot in a deployed position.

FIGS. 18-20 show the inner hemostatic assembly 90 with the beams 108, self-expanding plug 104' and optional sock constraint 136 in a collapsed form with the foot 122' not folded out. The foot 122' is mechanically connected to the rod 128 leading to the foot actuator 134 at the proximal end 94 of the elongate shaft 92. FIGS. 21 and 22 show how the foot embodiment 122' may be recessed and how it may be folded out and deployed. In this case the outer end 127 of the foot 122' points proximally when in a retracted state. When the foot 122' is folded out the thread 138 that is running through the hole 146 of the foot 122' is stretched and will be cut thus releasing the constraint of the sock constraint 136 from the self-expanding plug 104' as shown in the deployment sequence of FIGS. 37-39. A similar arrangement may be configured for releasable radial constraint of those self-expanding plug embodiments 104 wherein the foot 122 is disposed in a distally oriented retracted position as shown in FIGS. 14-17.

Figure 24:
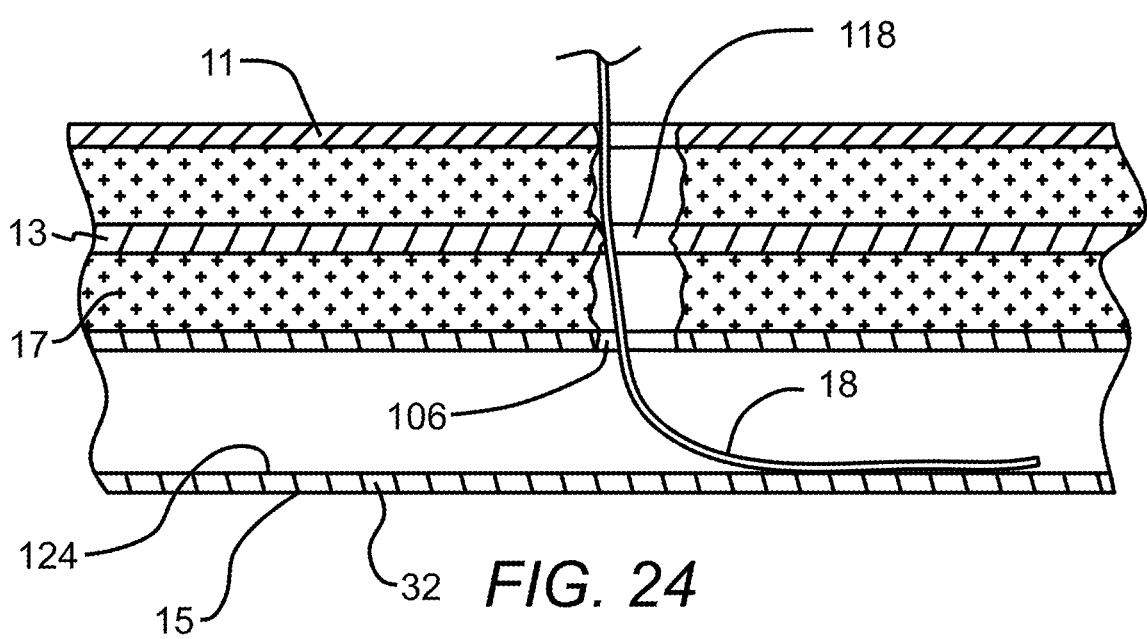
FIGS. 24-36 illustrate a sequence of a vascular closure method embodiment utilizing the vascular closure device embodiment of FIG. 5.
Figure 25:
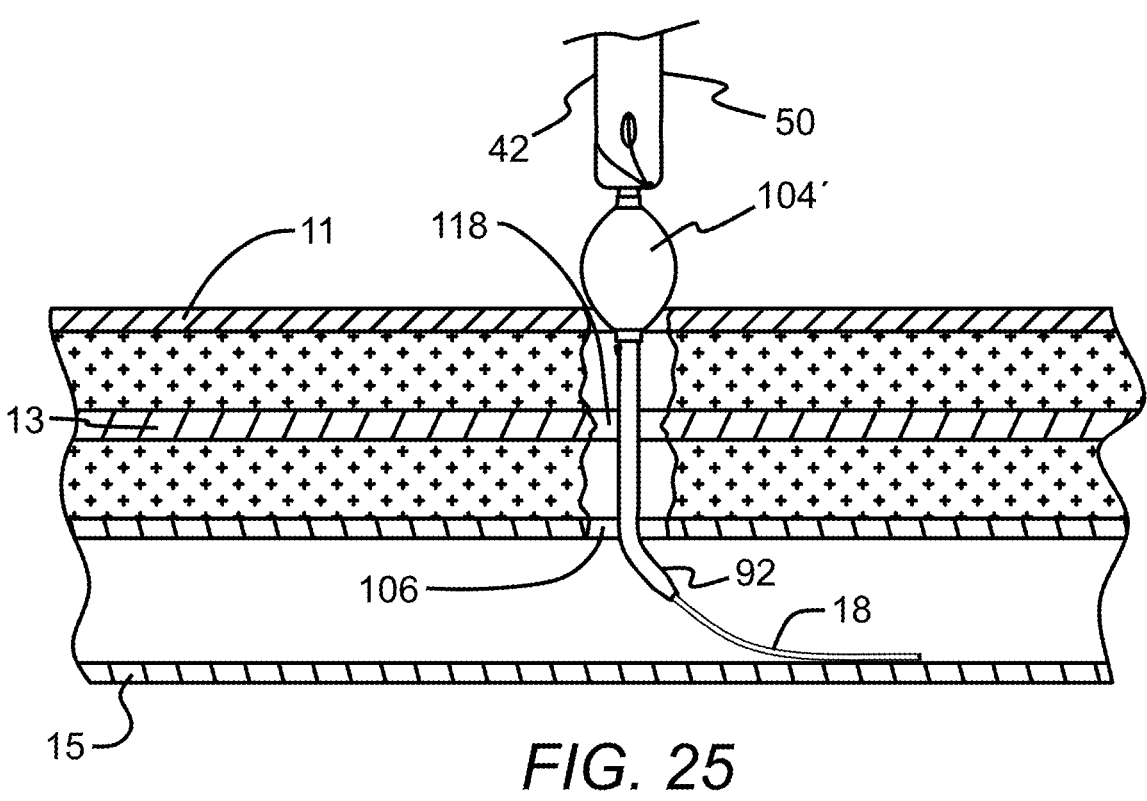
Figure 26:
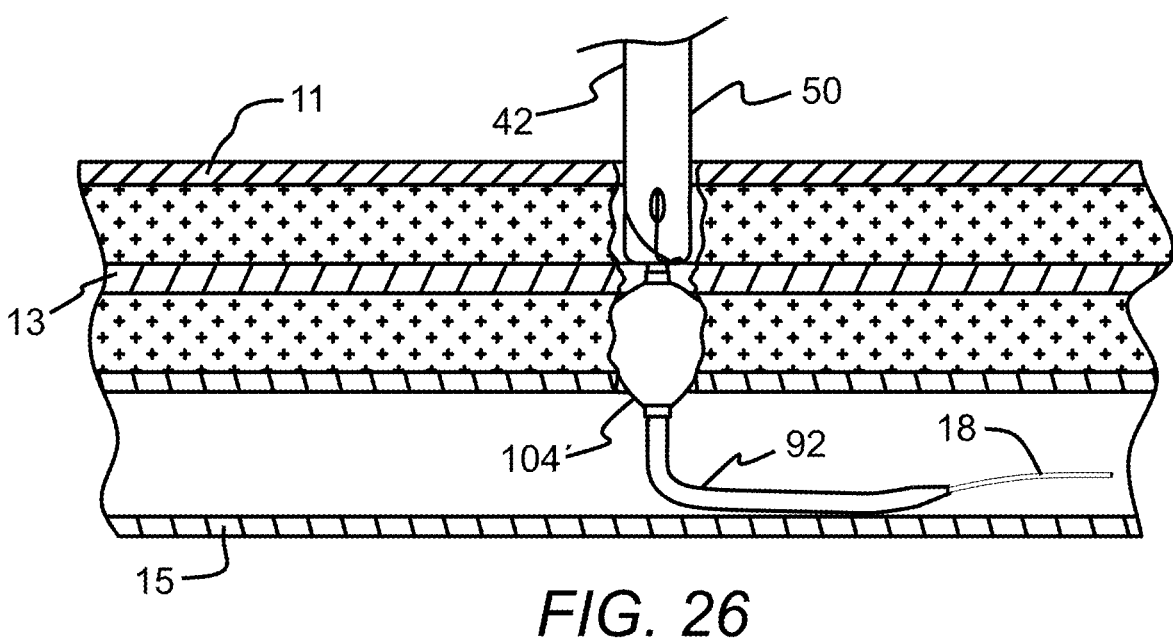

Referring to FIGS. 24-39, some embodiments of a method for closure of an access hole 106 in a vessel 15 of a patient may include advancing a guidewire 18 through a channel in the patient's skin 11 which may be contiguous with the passage 118 in fascia layer 13 and access hole 106 in the vessel 15 as shown in FIG. 24. The elongate shaft 92 of the inner hemostatic assembly 90 of the vascular closure device 40 may then be advanced over the guidewire 18 and through the passage 118 of the fascia 13 disposed adjacent access hole 106 and through the access hole 106 in the wall 32 of the patient's blood vessel 15 as shown in FIG. 25. The elongate shaft 92 may be so advanced until the distal end 96 of the elongate shaft 92 is disposed within the patient's vessel 15 and the self-expanding plug 104' disposed on a distal section 98 of the elongate shaft 92 is disposed adjacent the access hole 106 of the vessel 15 as shown in FIG. 26. The elongate shaft 92 may be so distally advanced with the self-expanding plug 104' in an expanded state thereby reducing leakage of blood from the access hole 106.

In some cases, an outside surface of the self-expanding plug 104' may be sealed against an outer portion or perimeter of the access hole 106 in the patient's blood vessel 15 in order to reduce leakage of blood from the access hole 106 in the vessel 15. Such self-expanding plug embodiments 104' may be integrated with vascular closure device embodiments 40 to be expanded from the location of the vessel wall 15 (but not inside of the vessel wall 15) through the fascia 13 thus filling up or otherwise sealing the access hole 106 in the vessel wall 32 partly (as the self-expanding plug 104' may be tapered) and fully at the level of the fascia 13.

In some cases, during axial positioning of the inner hemostatic assembly 90 and prior to sealing of the access hole 106, the self-expanding plug 104' may be disposed within the inner lumen 48 of the outer housing 42 in a compressed state, as shown in FIG. 7C. In some cases the self-expanding plug 104' may be so disposed within the inner lumen 48 in a constrained state as the elongate shaft 92 of the inner hemostatic assembly 90 is being advanced to position the self-expanding plug 104' adjacent the access hole 106. The self-expanding plug 104' may then be distally extended from the inner lumen 48 allowing the self-expanding plug to self-expand to the expanded state within or adjacent to the access hole 106 in the vessel 15 so as to seal against the access hole 106 and reduce or prevent leakage of blood from the access hole 106 as shown in FIG. 26.

Figure 37:
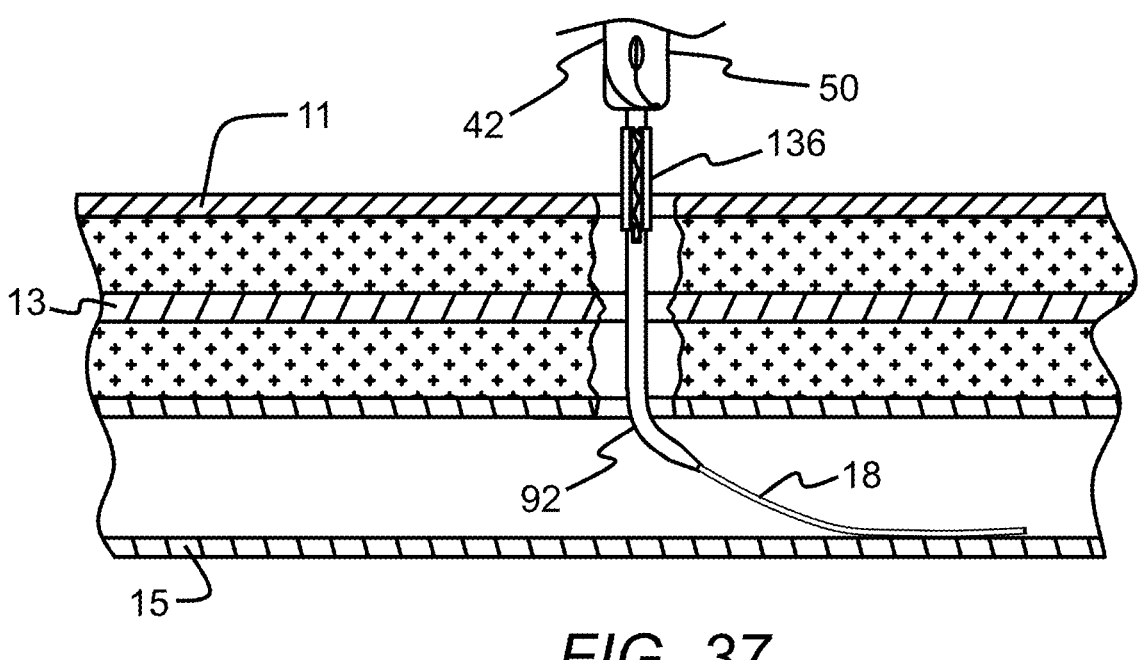
FIGS. 37-39 illustrate a sequence of deploying the self-expanding plug embodiment of the inner hemostatic assembly embodiment of FIGS. 18-23 by releasing the sock constraint which constrains the self-expanding plug embodiment.
Figure 38:
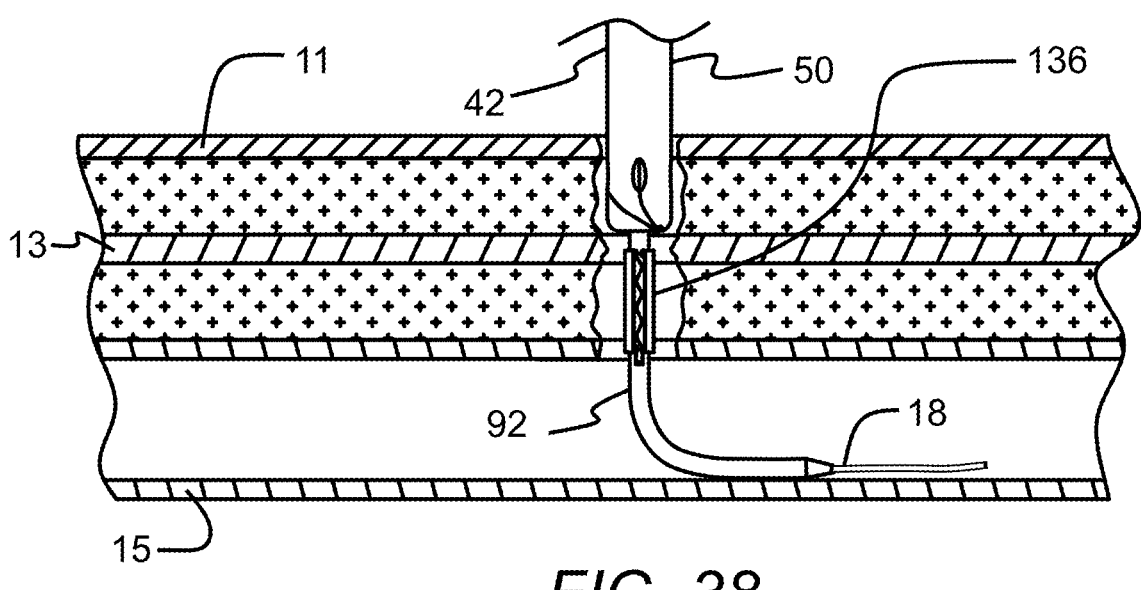
Figure 39:
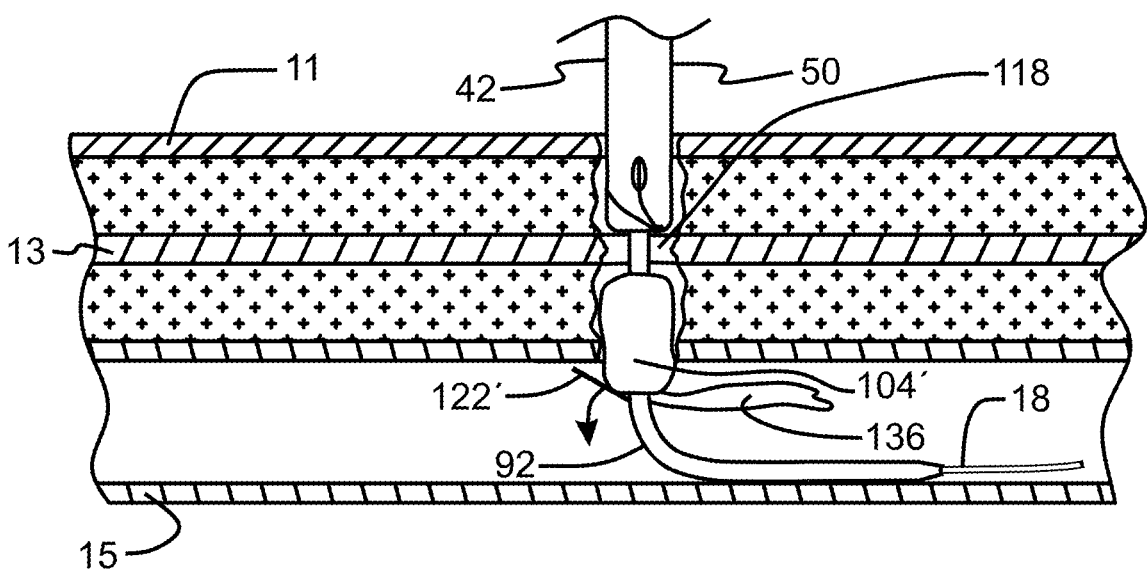

In other cases, the inner hemostatic assembly 90 may be advanced and positioned while the self-expanding plug 104' is maintained in a constrained state by the removable sock constraint 136 as shown in FIGS. 18-19. As shown in FIGS. 37-39, the elongate shaft 92 of the inner hemostatic assembly 90 may be advanced with the self-expanding plug 104' in a constrained state until the self-expanding plug 104' is disposed adjacent the access hole 106 as shown in FIG. 38. For such embodiments, the self-expanding plug 104' may then be released from the constrained state and allowed to expand into the expanded state by releasing the sock constraint 136 disposed over the self-expanding plug 104'. The sock constraint 136 may then be released from the self-expanding plug 104' and may hang freely thereafter except in the distal wall portion where the material of the sock constraint 136 is attached to the self-expanding plug 104' as shown in FIG. 39. In such methods, the self-expanding plug 104' expands from the constrained state to the unconstrained expanded state in close proximity to the access hole 106 and sealing against an outer perimeter of the access hole 106 thereby reducing leakage of blood from the access hole 106. For some embodiments, as discussed above, releasing the self-expanding plug 104' from the constrained state may include severing the thread 138 which secures the sock constraint 136 in the constrained state. For the embodiments shown in FIGS. 23, the thread 138 may be severed by axially translating the foot embodiment 122' that includes the hole 146 having a sharpened edge through which the thread 138 passes as shown by the arrow in FIG. 21A.

Figure 12:
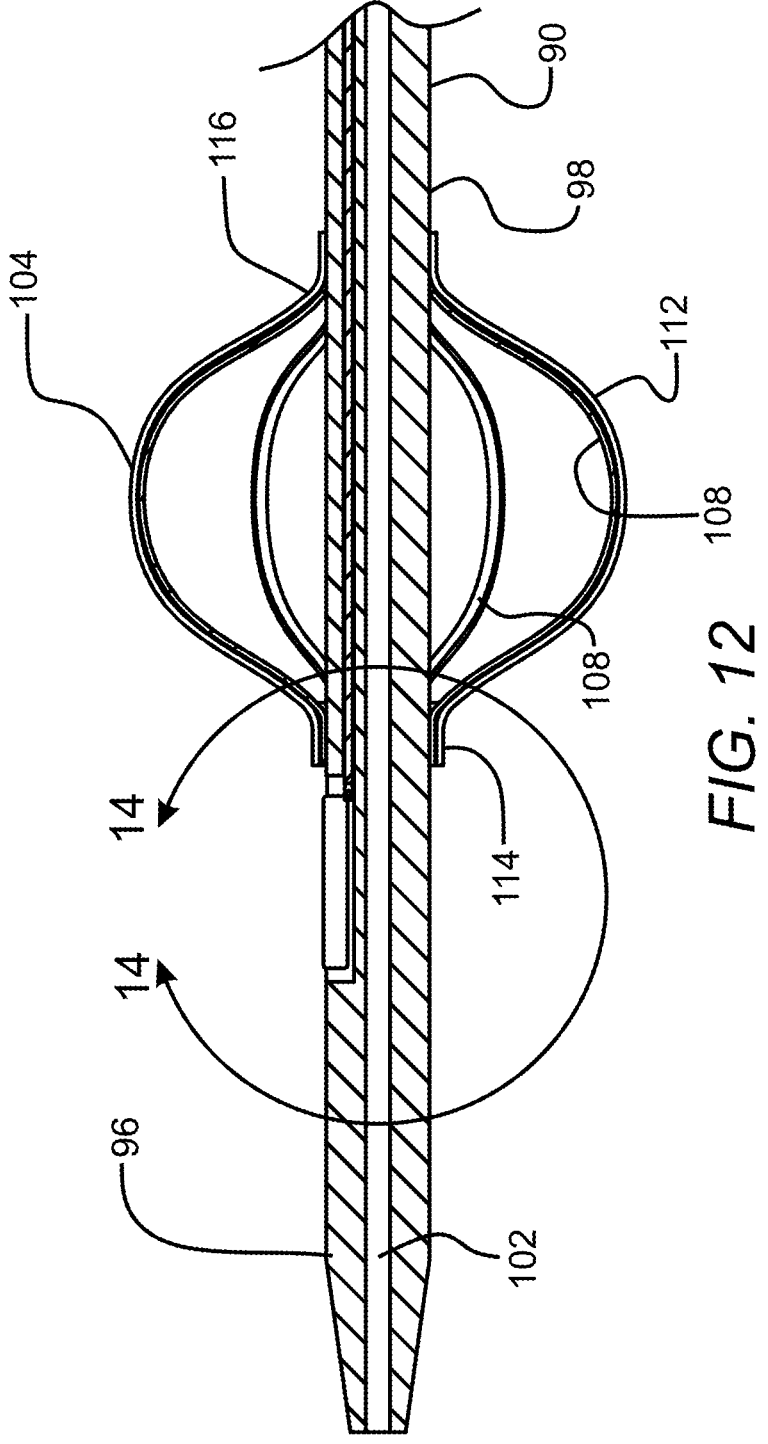
FIG. 12 is an enlarged view in longitudinal section of a distal section of the inner hemostatic assembly of FIG. 8 indicated by the encircled portion 12-12 of FIG. 8.
Figure 12A:
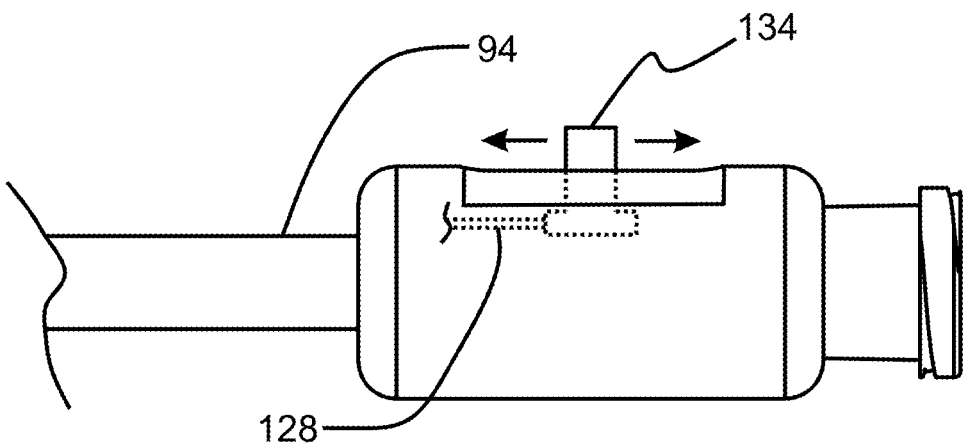
FIG. 12A is an enlarged view in partial section of a proximal section of the inner hemostatic assembly of FIG. 8 indicated by the encircled portion 12A-12A of FIG. 8.
Figure 27:
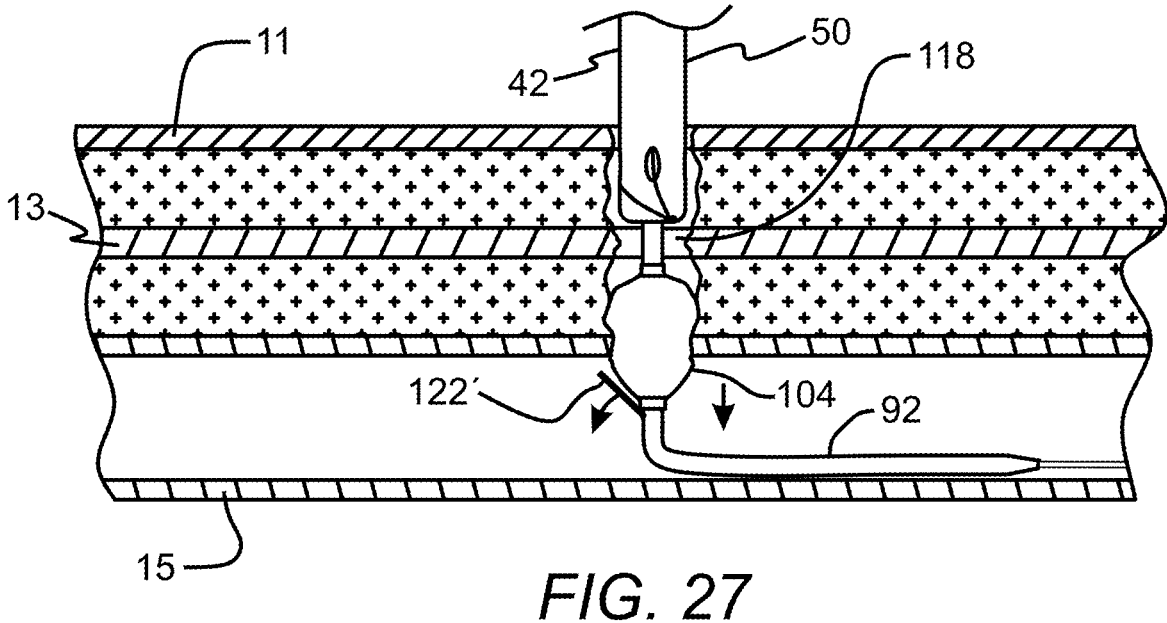

Once the inner hemostatic assembly 90 has been positioned with the self-expanding plug 104' disposed adjacent the access hole 106 to perform a sealing function as shown in FIG. 26, the inner hemostatic assembly 90 may be further distally advanced as shown in FIG. 27 in order to provide room for deployment of a device for axial position reference. As discussed above, some vascular closure device embodiments 40 include the lateral surface such as the foot 122' which may be configured to extend radially outward from the distal section 98 of the elongate shaft 92 distal of the self-expanding plug 104'. For such embodiments, the deployment method may include radially extending and deploying the foot 122' from the elongate shaft 92 while the foot 122' is disposed within the blood vessel 15 as shown in FIG. 27. The deployment method may include radially extending the hinged foot 122' by activating a foot actuator 134 which is operatively coupled to the hinged foot 122' as shown in FIG. 12A. The foot 122' is configured to provide a reference point between relative axial positions of the wall 32 of the blood vessel 15 and the self-expanding plug 104'. FIG. 28 shows the relation between the positions of the expanded self-expanding plug 104', the foot 122', the access hole 106 in the artery 15 and the passage in the fascia 13. The most distal part of the self-expanding plug 104' (and associated beams 108) may be generally axially coextensive with the base of the foot 122' generally in some cases. In this position, the expanded self-expanding plug 104' will substantially seal the access hole 106 in the arterial wall 32 as well as the access passage 118 in the fascia 13.

The method may further include positioning a distal end 46 of the outer housing 42 of the vascular closure device 40 adjacent the passage 118 in the fascia tissue layer 13 and deploying the plurality of anchor deployers 58 from the distal section 50 of the outer housing 42 of the vascular closure device 40 as shown in FIG. 29. In this view, the anchor deployers 58 are shown engaging the fascia tissue layer 13 in positions disposed about the access passage 118 in the tissue layer 13 with respective anchors 68 of the plurality of anchor deployers 58. In some instances, each of the plurality of anchors 68 may be deployed in a distal and radially outward direction from the distal section 50 of the outer housing 42.

Figure 30:
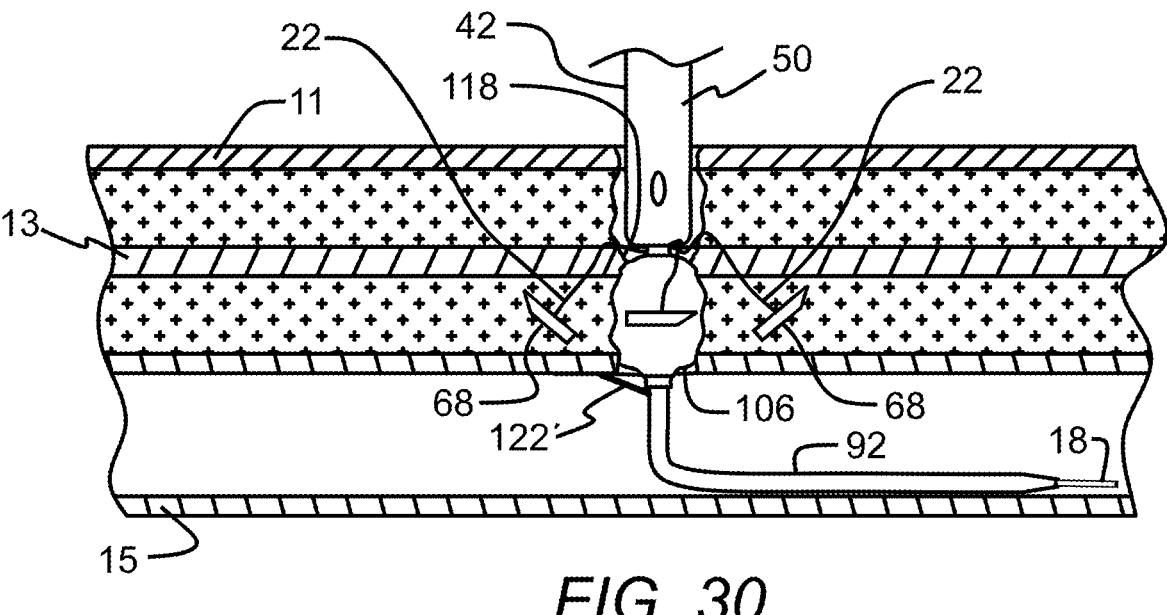

Once so deployed, the anchors 68 are secured to the tissue layer 13 in the positions disposed about the access passage 118 in the tissue layer 13. In some cases, the anchors 68 may be secured to the fascia tissue layer 13 by rotating or toggling the anchors 68 once they have been released from the distal end of the respective deployment rods 64 as shown in FIG. 30. Thereafter, the respective deployment rod 64 of each of the anchor deployers 58 may be proximally withdrawn back into the respective axial lumens 62 of the outer housing 42 as shown in FIG. 30. The anchors 68 are then drawn closer together with tension being applied to the filaments 72 secured to each of the anchors 68. The filaments 72 may be proximally withdrawn so as to draw the anchors 68 and respective portions of the tissue layer 13 secured to each of the anchors 68 together thereby reducing the passage 118 in the tissue layer 13 as shown in FIG. 31. For some embodiments, the filaments 72 may be proximally withdrawn by actuation of a filament tensioner 120 which is operatively coupled to a proximal portion (not shown) of each of the plurality of filaments 72 and which is disposed on the handle 54 shown in FIG. 5. In some cases, the filament tensioner 120 may be actuated by proximally retracting the filament tensioner 120 relative to the handle 54. In some cases, the filament tensioner 120 may include an elongate shaft slidably disposed within a lumen of the handle 54.

Figure 32:
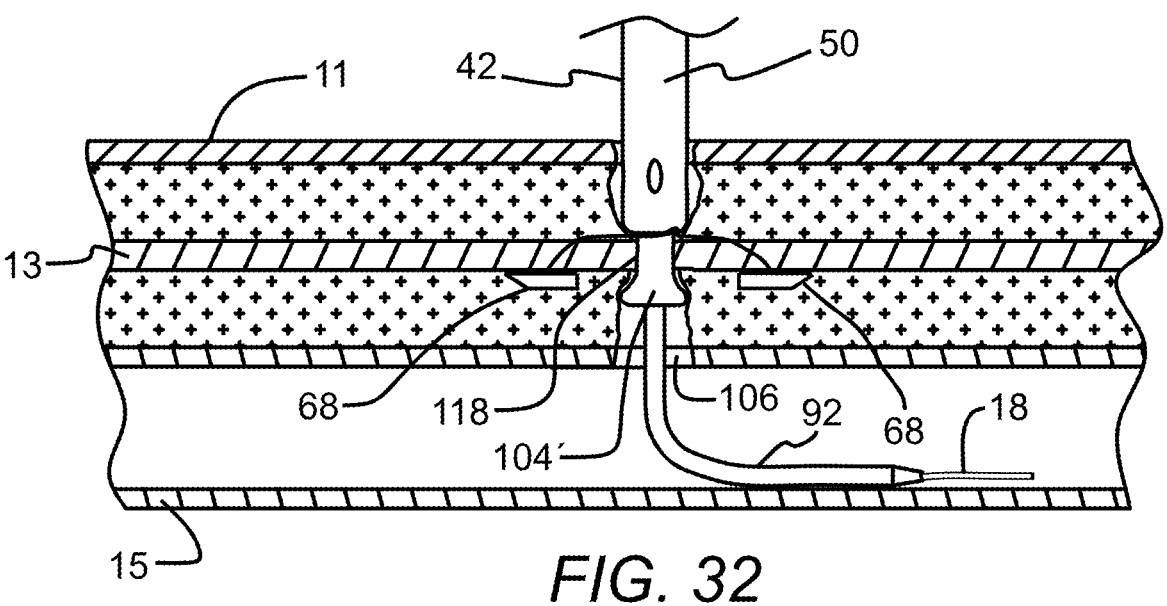
Figure 33:
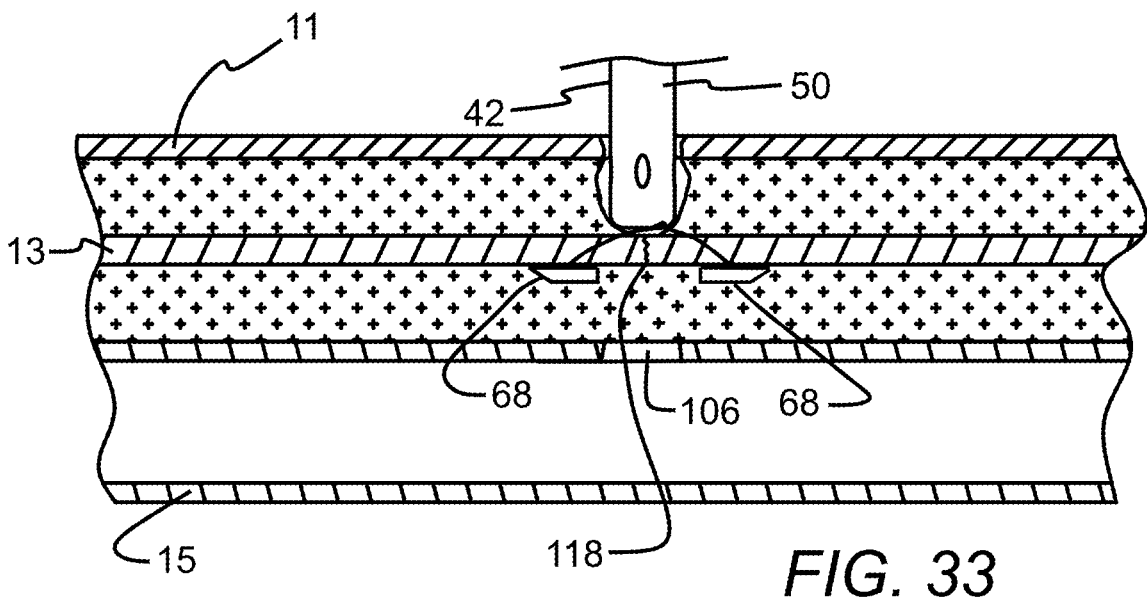

Thereafter, the foot 122' may be retracted as indicated by the arrow in FIG. 31 and the inner hemostatic assembly 90 may be withdrawn from the patient's vessel 15 and into the inner lumen 48 of the outer housing 42 until the elongate shaft 42 is no longer disposed within the access hole 106 of the vessel 15 or access passage 118 of the tissue layer 13 as shown in FIGS. 32 and 33. As filaments 72 of some vascular closure device embodiments 40 are tightened to close the access hole 118 in the fascia 13 and/or the vessel 15, some self-expanding plug embodiments 104' may be compressed radially (by a mechanism that depends on the specific design of the vascular closure device 40) in such a way that the self-expanding plug 104' can easily slip back in a proximal direction and not be trapped during closure of the access passageway 118. As such, when the inner hemostatic assembly 90 finally is ready for withdrawal the self-expanding plug 104' is intended to collapse when the inner hemostatic assembly 90 comes into the outer housing 42. The pre-curved shape of the beams 108 may be allowed to slide axially relative to the elongate shaft 92 to allow the curved shape of the beams 108 to compress as shown in FIG. 32 and not interfere with the withdrawal of the inner hemostatic assembly 90.

In some instances, the inner hemostatic assembly 90 may be proximally retracted simultaneously with the process of drawing the anchors 68 closer together with tension applied to the filaments 72, also as shown in FIG. 32. The guidewire 18 may also be proximally retracted from the access hole 106 and passage 118 in the fascia 13 as shown in FIG. 33.

A tissue grip may then be deployed to secure the portions of the tissue layer 13 which have been drawn together thereby closing the passage 118 in the tissue layer 13 and achieving vascular closure of the access hole 106 in the blood vessel 15. In some cases, as shown in FIGS. 34 and 35, deploying the tissue grip may include deploying the lock ring 86 onto the filaments 72. Deploying the lock ring embodiment 86 shown may include sliding the self-contracting lock ring 86 in an expanded state from the distal end 46 of the outer housing 42 over the filaments 72 and allowing the self-contracting lock ring 86 to contract to a relaxed state onto the filaments 72 thereby applying a compressive force onto the filaments 72 and holding them in fixed relation to each other as shown in FIG. 35.

Figure 36:
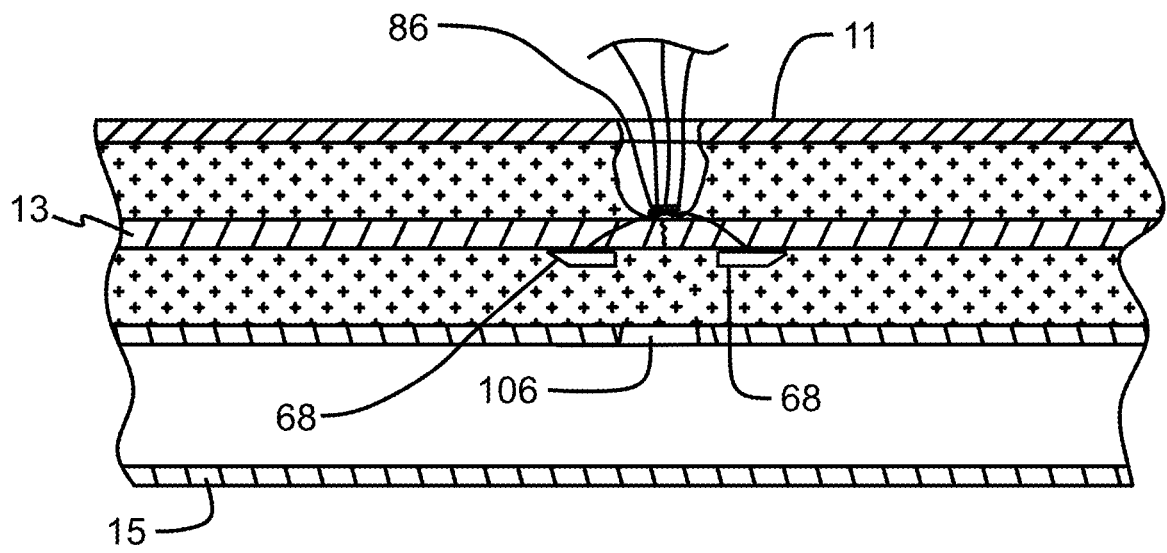

For the embodiment shown, the lock ring 86 is deployed by retracting the filament tube 78 proximally within the lumen 82 of the outer housing 42 such that the lock ring 86 is forced from the distal end 80 of the filament tube 78 and onto the filaments 72 disposed within the inner lumen 82 of the filament tube 78 as shown in FIG. 35. In some cases, deploying the tissue grip may include deploying a tissue adhesive (not shown) onto the portions of the tissue layer 13 that have been drawn together by the anchors 68. In some instances, applying a tissue adhesive to the portions of the tissue layer 13 that have been drawn together by the anchors 72 may include applying cyanoacrylate adhesive to the portions of the tissue layer 13 that have been drawn together by the anchors 68. Thereafter, the vascular closure device 40 may be proximally withdrawn from the closure site completely as shown in FIG. 36. The filaments 68 may then be trimmed if desired and the skin layer 11 suitably closed.

Embodiments illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation and use of such terms and expressions do not exclude any equivalents of the features shown and described or portions thereof, and various modifications are possible. The term "a" or "an" can refer to one of or a plurality of the elements it modifies (e.g., "a reagent" can mean one or more reagents) unless it is contextually clear either one of the elements or more than one of the elements is described. Thus, it should be understood that although embodiments have been specifically disclosed by representative embodiments and optional features, modification and variation of the concepts herein disclosed may be resorted to by those skilled in the art, and such modifications and variations are considered within the scope of this disclosure.

With regard to the above detailed description, like reference numerals used therein refer to like elements that may have the same or similar dimensions, materials and configurations. While particular forms of embodiments have been illustrated and described, it will be apparent that various modifications can be made without departing from the spirit and scope of the embodiments of the invention. Accordingly, it is not intended that the invention be limited by the forgoing detailed description.

What is claimed is:

1. A method for vascular closure, comprising:

advancing an elongate shaft of an inner hemostatic assembly of a vascular closure device over a guidewire and through a passage in a tissue layer which is disposed adjacent an access hole in a wall of a patient's blood vessel until a distal end of the elongate shaft is disposed within the patient's vessel and a self-expanding plug disposed on a distal section of the elongate shaft is disposed within the access hole in an expanded state and is reducing leakage of blood from the access hole;

positioning a distal end of an outer housing of the vascular closure device adjacent the passage in the tissue layer;

deploying a plurality of anchor deployers from a distal section of the outer housing of the vascular closure device and engaging the tissue layer in positions disposed about the passage in the tissue layer with respective anchors of the plurality of anchor deployers;

securing the anchors to the tissue layer in the positions disposed about the passage in the tissue layer;

drawing the anchors closer together with filaments secured to each of the anchors so as to draw the anchors and respective portions of the tissue layer secured to each of the anchors together thereby reducing the passage in the tissue layer;

proximally withdrawing the inner hemostatic assembly from the patient's vessel and into the inner lumen of the outer housing until the elongate shaft is no longer disposed within the access hole of the vessel or passage of the tissue layer; and deploying a tissue grip to secure the portions of the tissue layer which have been drawn together thereby closing the passage in the tissue layer and achieving vascular closure of the access hole in the blood vessel, wherein the vascular closure device further comprises a lateral surface configured to extend radially from a distal section of the elongate shaft distal of the self-expanding plug and further comprising radially extending the lateral surface from the elongate shaft while the lateral surface is disposed within the blood vessel to provide a reference point between relative axial positions of the wall of the blood vessel and the self-expanding plug.

2. The method of claim 1 wherein the inner hemostatic assembly is proximally retracted simultaneously with drawing the anchors closer together with the filaments.

3. The method of claim 1 further comprising proximally retracting the guidewire from the access hole and passage.

4. The method of claim 1 wherein the self-expanding plug is disposed within the inner lumen of the outer housing in a compressed state as the elongate shaft of the inner hemostatic assembly is being advanced and further comprising distally extending the self-expanding plug from the inner lumen and allowing the self-expanding plug to self-expand to the expanded state within the access hole.

5. The method of claim 1 wherein the self-expanding plug is sealed against the access hole in the patient's blood vessel.

6. The method of claim 1 wherein each of the plurality of anchors is deployed in a distal and radially outward direction from the distal section of the outer housing.

7. The method of claim 1 wherein deploying the tissue grip comprises deploying a tissue adhesive onto the portions of the tissue layer that have been drawn together by the anchors.

8. The method of claim 1 wherein applying a tissue adhesive to the portions of the tissue layer that have been drawn together by the anchors comprises applying cyanoacrylate adhesive to the portions of the tissue layer that have been drawn together by the anchors.

9. The method of claim 1 wherein deploying the tissue grip comprises deploying a lock ring onto the filaments.

10. The method of claim 9 wherein deploying the lock ring comprises sliding a self-contracting lock ring in an expanded state from a distal end of the housing over the filaments and allowing the self-contracting lock ring to contract to a relaxed state over the filaments.

11. The method of claim 1 wherein the elongate shaft of the inner hemostatic assembly is advanced with the self-expanding plug in a constrained state until the self-expanding plug is disposed within the access hole and further comprising releasing the self-expanding plug from the constrained state into the expanded state by releasing a constraint sock disposed over the self-expanding plug from a constrained state to an unconstrained state thereby reducing leakage of blood from the access hole.

12. The method of claim 11 wherein releasing the self-expanding plug from the constrained state comprises severing a thread which secures the constraint sock in the constrained state.

13. The method of claim 1 wherein the lateral surface comprises a hinged foot with an inner end pivotally secured to the elongate shaft and radially extending the hinged foot comprises activating a foot actuator which is operatively coupled to the hinged foot.

* * * * *

18